(12) United States Patent
Hansen et al.

(10) Patent No.: US 8,486,890 B2
(45) Date of Patent: Jul. 16, 2013

(54) AMYLIN DERIVATIVES

(75) Inventors: Thomas Kruse Hansen, Herlev (DK); Lauge Schäffer, Lyngby (DK); Jesper Lau, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 443 days.

(21) Appl. No.: 12/282,042

(22) PCT Filed: Mar. 15, 2007

(86) PCT No.: PCT/EP2007/052456
§ 371 (c)(1),
(2), (4) Date: Nov. 13, 2008

(87) PCT Pub. No.: WO2007/104789
PCT Pub. Date: Sep. 20, 2007

(65) Prior Publication Data
US 2009/0099085 A1 Apr. 16, 2009

(30) Foreign Application Priority Data
Mar. 15, 2006 (EP) .................................. 06111172

(51) Int. Cl.
*A61K 38/26* (2006.01)
*A61K 38/00* (2006.01)
*A61P 3/10* (2006.01)

(52) U.S. Cl.
USPC .............. 514/11.7; 514/1.1; 514/6.8; 514/6.9

(58) Field of Classification Search
None
See application file for complete search history.

(56) References Cited

U.S. PATENT DOCUMENTS

| | | | |
|---|---|---|---|
| 5,710,024 | A | 1/1998 | Adamou et al. |
| 2003/0130177 | A1 * | 7/2003 | Kolterman et al. ............... 514/9 |
| 2004/0022807 | A1 | 2/2004 | Duft et al. |
| 2009/0099085 | A1 | 4/2009 | Hansen et al. |
| 2010/0222269 | A1 | 9/2010 | Schaffer et al. |
| 2011/0105394 | A1 | 5/2011 | Schaffer et al. |

FOREIGN PATENT DOCUMENTS

| | | |
|---|---|---|
| WO | WO 93/10147 | 5/1993 |
| WO | WO 01/45746 | 6/2001 |
| WO | WO 2005/027978 | 3/2005 |
| WO | WO 2005/028516 | 3/2005 |
| WO | WO 2005/077072 | 8/2005 |
| WO | WO 2005/097202 | 10/2005 |
| WO | WO 2005/118642 | 12/2005 |
| WO | WO 2006/005667 | 1/2006 |
| WO | WO 2006/059106 | 6/2006 |
| WO | WO 2006/105345 | 10/2006 |
| WO | 2007/055728 A1 | 5/2007 |
| WO | 2007/109354 A2 | 9/2007 |
| WO | WO 2007/104789 | 9/2007 |
| WO | WO 2009/034119 | 3/2009 |
| WO | WO 2010/046357 | 4/2010 |

OTHER PUBLICATIONS

Veronese, Biomaterials 22: 405-417, 2001.*
Holz, G.G., et al, Current Medicinal Chemistry, 2003, pp. 2471-2483, vol. 10, Part 22.
Wan, L., et al, Journal of Pharmaceutical Scienes, 2003, pp. 1882-1892, vol. 92, Part 9.
Kurtzhals, P., International Journal of Obesity, 2004, pp. S23-S28, vol. 28, Part 2.
Colburn, W.A., J Clin Pharmacol, 1996, pp. 13-24, vol. 36.
Definition of Moiety http://dictionary.reference.com/browse/moiety, pp. 1-3. Accessed Aug. 26, 2010.
Andrew Young, Advances in Pharmacology, 2005, vol. 52, pp. 1-18.
Broadhead et al., Drug Development and Industrial Pharmacy, "The Spray Drying of Pharmaceuticals", 1992, vol. 18, Part 11-12, pp. 1169-1206.
Chien, Jianweiyu and Yie, Critical Reviews in Therapeutic Drug Carrier, "Pulmonary Drug Delivery: Physiologic and Mechanistic Aspect" 1997, vol. 14, Part 4, pp. 395-453.
Carpenter and Crowe, Cryobiology, "Modes of Stabilization of a Protein by Organic Solutes During Dessication", 1998, vol. 25, pp. 459-470.
Kurtzhals, P et al., Biochemical Journal, "Albumin Binding of Insulins Acylated With Fatty Acides . . . " 1995, vol. 312, pp. 725-731.
Mumenthaler et al., Pharmaceutical Research, "Feasibility Study on Spray-Drying Protein Pharmaceuticals: Recombinant Human Growth Hormane and Tissue-Type Plasminogen Activator", 1994, vol. 11, Part 1, pp. 12-20.
Roser, Biopharmaceutical, "Trehalsoe Drying: a Novel Replacement for Freeze Drying" 1991, vol. 4, pp. 47-53.
William and Polli, J. Parenteral Sci. Technol. " " 1984, vol. 38, pp. 48-59.
Spray Drying Handbook, 1991, pp. 491-676.
Dennis M.S. et al., Journal of Biological Chemistry; "Albumin Binding as a General Strategy for Improving the Pharmacokinetics of Proteins"; 2002, vol. 277, No. 38, pp. 35035-35043.
Holz, George G., et al, "Glucagon-Like Peptide-1 Synthetic Analogs: New Therapeutic Agents for Use in the Treatment of Diabetes Mellitus," Curr Med Chem (2003), vol. 10, No. 22, pp. 2471-2483.
Yan, L M et al. "Design of a Mimic of Nonamyloidogenic" Proceedings of the National Academy of Sciences, 2006, vol. 103 (7), pp. 2046-2051.

\* cited by examiner

*Primary Examiner* — Gyan Chandra
(74) *Attorney, Agent, or Firm* — Jianjie Hu

(57) ABSTRACT

The present invention relates to novel amylin derivatives having a protracted action profile, to pharmaceutical compositions comprising these derivatives and to the use of the derivatives for the treatment of diseases related to obesity, diabetes and other metabolic disorders.

9 Claims, No Drawings

```
                        SEQUENCE LISTING

<160> NUMBER OF SEQ ID NOS: 24

<210> SEQ ID NO 1
<211> LENGTH: 37
<212> TYPE: PRT
<213> ORGANISM: Homo sapiens
<220> FEATURE:
<221> NAME/KEY: DISULFID
<222> LOCATION: (2)..(7)

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 7
<212> TYPE: PRT
<213> ORGANISM: Artificial
<220> FEATURE:
<223> OTHER INFORMATION: Amylin sequence or derivative

<400> SEQUENCE: 2

Phe Gly Ala Ile Leu Ser Ser
1               5

<210> SEQ ID NO 3
<211> LENGTH: 7
<212> TYPE: PRT
<213> ORGANISM: Artificial
<220> FEATURE:
<223> OTHER INFORMATION: Amylin sequence or derivative

<400> SEQUENCE: 3

Phe Gly Pro Ile Leu Pro Pro
1               5

<210> SEQ ID NO 4
<211> LENGTH: 7
<212> TYPE: PRT
<213> ORGANISM: Artificial
<220> FEATURE:
<223> OTHER INFORMATION: Amylin sequence or derivative

<400> SEQUENCE: 4

Phe Gly Glu Ile Leu Ser Ser
1               5

<210> SEQ ID NO 5
<211> LENGTH: 7
<212> TYPE: PRT
<213> ORGANISM: artificial
<220> FEATURE:
<223> OTHER INFORMATION: Amylin sequence or derivative

<400> SEQUENCE: 5
```

-continued

```
Phe Gly Asp Ile Leu Ser Ser
1               5

<210> SEQ ID NO 6
<211> LENGTH: 37
<212> TYPE: PRT
<213> ORGANISM: artificial
<220> FEATURE:
<223> OTHER INFORMATION: Amylin sequence or derivative

<400> SEQUENCE: 6

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Lys Val
            20                  25                  30

Gly Ser Asn Thr Tyr
        35

<210> SEQ ID NO 7
<211> LENGTH: 38
<212> TYPE: PRT
<213> ORGANISM: artificial
<220> FEATURE:
<223> OTHER INFORMATION: Amylin sequence or derivative

<400> SEQUENCE: 7

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr Lys
        35

<210> SEQ ID NO 8
<211> LENGTH: 37
<212> TYPE: PRT
<213> ORGANISM: artificial
<220> FEATURE:
<223> OTHER INFORMATION: Amylin sequence or derivative

<400> SEQUENCE: 8

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Lys Pro Thr Asn Val
            20                  25                  30

Gly Ser Asn Thr Tyr
        35

<210> SEQ ID NO 9
<211> LENGTH: 37
<212> TYPE: PRT
<213> ORGANISM: artificial
<220> FEATURE:
<223> OTHER INFORMATION: Amylin sequence or derivative

<400> SEQUENCE: 9

Lys Cys Asn Thr Ala Thr Cys Ala Thr Gln Lys Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35
```

```
<210> SEQ ID NO 10
<211> LENGTH: 37
<212> TYPE: PRT
<213> ORGANISM: artificial
<220> FEATURE:
<223> OTHER INFORMATION: Amylin sequence or derivative

<400> SEQUENCE: 10

Lys Cys Asn Thr Ala Thr Cys Ala Thr Gln Arg Leu Ala Asn Phe Leu
1               5                   10                  15

Val His Ser Ser Lys Asn Phe Gly Pro Ile Leu Pro Pro Thr Asn Val
            20                  25                  30

Gly Ser Asn Thr Tyr
        35

<210> SEQ ID NO 11
<211> LENGTH: 37
<212> TYPE: PRT
<213> ORGANISM: artificial
<220> FEATURE:
<223> OTHER INFORMATION: Amylin sequence or derivative

<400> SEQUENCE: 11

Lys Cys Asn Thr Ala Thr Cys Ala Thr Gln Arg Leu Ala Asn Phe Leu
1               5                   10                  15

Val His Ser Ser Asn Lys Phe Gly Pro Ile Leu Pro Pro Thr Asn Val
            20                  25                  30

Gly Ser Asn Thr Tyr
        35

<210> SEQ ID NO 12
<211> LENGTH: 37
<212> TYPE: PRT
<213> ORGANISM: artificial
<220> FEATURE:
<223> OTHER INFORMATION: Amylin sequence or derivative

<400> SEQUENCE: 12

Lys Cys Asn Thr Ala Thr Cys Ala Thr Gln Arg Leu Ala Asn Phe Lys
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 13
<211> LENGTH: 37
<212> TYPE: PRT
<213> ORGANISM: artificial
<220> FEATURE:
<223> OTHER INFORMATION: Amylin sequence or derivative

<400> SEQUENCE: 13

Lys Cys Asn Thr Ala Thr Cys Ala Thr Gln Arg Leu Ala Asn Phe Leu
1               5                   10                  15

Lys His Ser Ser Asn Asn Phe Gly Pro Ile Leu Pro Pro Thr Asn Val
            20                  25                  30

Gly Ser Asn Thr Tyr
        35

<210> SEQ ID NO 14
<211> LENGTH: 37
<212> TYPE: PRT
<213> ORGANISM: artificial
```

```
<220> FEATURE:
<223> OTHER INFORMATION: Amylin sequence or derivative

<400> SEQUENCE: 14

Lys Cys Asn Thr Ala Thr Cys Ala Thr Gln Arg Leu Ala Lys Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 15
<211> LENGTH: 37
<212> TYPE: PRT
<213> ORGANISM: artificial
<220> FEATURE:
<223> OTHER INFORMATION: Amylin sequence or derivative

<400> SEQUENCE: 15

Lys Cys Asn Thr Ala Thr Cys Ala Thr Gln Arg Leu Ala Asn Lys Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 16
<211> LENGTH: 37
<212> TYPE: PRT
<213> ORGANISM: artificial
<220> FEATURE:
<223> OTHER INFORMATION: Amylin sequence or derivative

<400> SEQUENCE: 16

Lys Cys Asn Thr Ala Thr Cys Ala Thr Lys Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 17
<211> LENGTH: 37
<212> TYPE: PRT
<213> ORGANISM: artificial
<220> FEATURE:
<223> OTHER INFORMATION: Amylin sequence or derivative

<400> SEQUENCE: 17

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Lys Thr Tyr
        35

<210> SEQ ID NO 18
<211> LENGTH: 38
<212> TYPE: PRT
<213> ORGANISM: artificial
<220> FEATURE:
<223> OTHER INFORMATION: Amylin sequence or derivative

<400> SEQUENCE: 18
```

```
Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr Lys
            35

<210> SEQ ID NO 19
<211> LENGTH: 37
<212> TYPE: PRT
<213> ORGANISM: artificial
<220> FEATURE:
<223> OTHER INFORMATION: Amylin sequence or derivative

<400> SEQUENCE: 19

Lys Cys Asn Thr Ala Thr Cys Ala Thr Gln Arg Leu Ala Asn Phe Leu
1               5                   10                  15

Val Lys Ser Ser Asn Asn Phe Gly Pro Ile Leu Pro Pro Thr Asn Val
            20                  25                  30

Gly Ser Asn Thr Tyr
            35

<210> SEQ ID NO 20
<211> LENGTH: 37
<212> TYPE: PRT
<213> ORGANISM: artificial
<220> FEATURE:
<223> OTHER INFORMATION: Amylin sequence or derivative

<400> SEQUENCE: 20

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Lys Thr Asn Val
            20                  25                  30

Gly Ser Asn Thr Tyr
            35

<210> SEQ ID NO 21
<211> LENGTH: 37
<212> TYPE: PRT
<213> ORGANISM: artificial
<220> FEATURE:
<223> OTHER INFORMATION: Amylin sequence or derivative

<400> SEQUENCE: 21

Lys Cys Asn Thr Ala Thr Cys Ala Thr Gln Arg Leu Ala Asn Phe Leu
1               5                   10                  15

Val Lys Ser Ser Asn Asn Leu Gly Pro Val Leu Pro Pro Thr Asn Val
            20                  25                  30

Gly Ser Asn Thr Tyr
            35

<210> SEQ ID NO 22
<211> LENGTH: 37
<212> TYPE: PRT
<213> ORGANISM: artificial
<220> FEATURE:
<223> OTHER INFORMATION: Amylin sequence or derivative

<400> SEQUENCE: 22

Lys Cys Asn Thr Ala Thr Cys Ala Thr Gln Lys Leu Ala Asn Phe Leu
1               5                   10                  15
```

```
Val Arg Ser Ser Asn Asn Leu Gly Pro Val Leu Pro Pro Thr Asn Val
            20                  25                  30

Gly Ser Asn Thr Tyr
        35

<210> SEQ ID NO 23
<211> LENGTH: 37
<212> TYPE: PRT
<213> ORGANISM: artificial
<220> FEATURE:
<223> OTHER INFORMATION: Amylin sequence or derivative

<400> SEQUENCE: 23

Lys Cys Asn Thr Ala Thr Cys Ala Thr Gln Arg Leu Ala Asn Phe Leu
1               5                   10                  15

Val His Ser Ser Asn Asn Phe Gly Lys Ile Leu Pro Pro Thr Asn Val
            20                  25                  30

Gly Ser Asn Thr Tyr
        35

<210> SEQ ID NO 24
<211> LENGTH: 37
<212> TYPE: PRT
<213> ORGANISM: artificial
<220> FEATURE:
<223> OTHER INFORMATION: Amylin sequence or derivative

<400> SEQUENCE: 24

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35
```

AMYLIN DERIVATIVES

CROSS-REFERENCE TO RELATED APPLICATIONS

This application is a 35 U.S.C. §371 national stage application of International Patent Application PCT/EP2007/052456 (published as WO 2007/104789 A2), filed Mar. 15, 2007, which claimed priority of European Patent Application 06111172.0, filed Mar. 15, 2006.

FIELD OF THE INVENTION

The present invention relates to novel amylin derivatives, to pharmaceutical compositions comprising these derivatives and to the use of the derivatives for the treatment of diseases related to obesity, diabetes and other metabolic disorders.

BACKGROUND OF THE INVENTION

A large and growing number of people suffer from diabetes mellitus and obesity. Diabetes mellitus is a metabolic disorder in which the ability to utilize glucose is partly or completely lost. About 5% of all people suffer from diabetes and the disorder approaches epidemic proportions. Since the introduction of insulin in the 1920's, continuous efforts have been made to improve the treatment of diabetes mellitus.

The two conditions diabetes mellitus and obesity are related in the sense that diabetes is common among obese patients and vice versa. There is also a strong link between diabetes mellitus and obesity on one side and cardio-vascular diseases on the other. This leads to a shorter life span for people suffering from these conditions. It is well-known and documented that effective treatment of diabetes mellitus and obesity lead to fewer complications such as diabetic late-complications affecting e.g. vision and kidney function.

A number of treatment regimes are targeting excessive blood glucose whereas others are focused primarily on weight reduction. The most efficient anti-diabetic agent used to lower blood glucose is insulin and analog(s) thereof. It has been known for a long time that when traditional insulin is used to treat diabetes, it is associated with an increase in body weight. Insulin has to be injected subcutaneously up to several times per day.

Type 2 diabetes is generally treated in the early phases with diet and exercise. As the condition progresses, various oral anti-diabetic agents are added. Injected agents such as GLP-1 analogs may also be used at this stage. In general, these agents are most efficient in patients with functioning beta-cells capable of releasing insulin and amylin. In 95% of progressed type 2 diabetes patients' amylin precipitates in the pancreas and may constitute a cause of the final beta-cell failure (L. Yan, PNAS, 2006, 103(7), 2046-2051). Ultimately, the patient is no longer able to produce amylin and insulin. Like Type 1-diabetic patients, these progressed Type-2 diabetic patients are then treated with insulin in spite of the fact that the beta-cell actually produces two hormones amylin and insulin. Only very recently, it has become possible to substitute amylin as well as insulin.

Human amylin is a 37 amino acid long peptide which has physico-chemical properties that make its use as a drug troublesome. In particular, it has a tendency to fibrillate in-vitro and/or ex-vivo and become ineffective due to precipitation. A drug product called Symlin is currently on the market which contains an analog of human amylin (pramlintide) where three of the 37 amino acids are substituted to proline. This improves substantially the fibrillating tendency. However, even pramlintide is difficult to keep in solution at neutral pH and it is therefore provided in an acidic solution i.e. Symlin.

The actions of amylin in relation to diabetes and obesity are: Reduction of food intake leading to lower bodyweight, slower gastric emptying, smoothening of post-prandial glucose profiles, and a reduction in the excessive diabetic glucagon release (A. Young, Amylin: Physiology and Pharmacology, Academic Press (2005)). By and large the actions of amylin are mediated via identified CNS receptors rather than directly on the target organs.

Symlin is approved as an adjunct drug with insulin. Clinical trials have revealed improved HbA1c in the order of 0.3-0.6, a smoother and shallower post-prandial blood glucose profile and reduction in body weight in contrast to treatment with insulin alone. Symlin is currently administered as a separate injection at a separate injection site three times daily. If the patient also uses three insulin injections per day, this adds up to a total of six daily injections.

Symlin therapy is limited by nausea as a side-effect. The nausea is dose-related, but has a tendency to diminish with time. The pharmaco-kinetic profile of Symlin leads to rather large variations in plasma levels throughout the day. It takes approximately 20 minutes after a subcutaneous injection for Symlin to reach $C_{max}$, and plasma t½ is in the order of 20-50 minutes (Colburn, W. A. J. Clin. Pharmacol. 36, 13-24 (1996). Ultimately, this leads to a need for three or more daily injections of Symlin in order to keep pharmacological plasma level without substantial side-effects. Even with three daily injections Symlin does not mimic the natural release profile of amylin very well. Amylin is released as meal related peaks with a duration close to 3-6 hours in contrast to the 1-1½ hour duration of an injected Symlin profile. Amylin also has a substantial basal level that is not mimicked by Symlin (A. Young, Amylin: Physiology and Pharmacology, Academic Press (2005)).

Type-1 diabetic patients are essentially without natural release of amylin and type-2 patients have lower levels than healthy individuals.

It would be useful to provide derivatives that have the activities of native human amylin, as well as derivatives which have a protracted PK-profile, show enhanced solubility and/or stability over native human amylin.

SUMMARY OF THE INVENTION

The invention relates in one aspect to a compound which is a derivative of human amylin with SEQ ID No 1 or an analog thereof, wherein
 a) an amino acid residue in position 2 to 37 has been substituted with a lysine residue or a cysteine residue, wherein the lysine residue or cysteine residue is linked to an albumin binding residue or a polyethylene glycol polymer, or
 b) the lysine residue in position 1 is linked to an albumin binding residue or a polyethylene glycol polymer, or
 c) a lysine residue has been added in position 38 and wherein said lysine residue is linked to an albumin binding residue or a polyethylene glycol polymer
optionally via a linker;
wherein the amino acid numbering conforms with the amino acid numbering shown in SEQ ID No 1.

The invention relates in one aspect to a compound which is a derivative of human amylin with SEQ ID No. 1 or an analog thereof, wherein
 a) an amino acid residue in position 2 to 37 has been substituted with a lysine residue or a cysteine residue, wherein the lysine residue or cysteine residue is linked to an albumin binding residue or a polyethylene glycol polymer, or b) the lysine residue in position 1 is linked to an albumin binding residue or a polyethylene glycol polymer, optionally via a linker; wherein the amino acid numbering conforms with the amino acid numbering in SEQ ID No 1.

The present invention also provides a method for increasing the time of action in a patient of human amylin or an analog thereof, characterized by a) modifying an amino acid residue in position 2 to 37 by substitution with a lysine residue or a cysteine residue and by linking said lysine residue or cysteine residue to an albumin binding residue or a polyethylene glycol polymer, or b) linking the lysine residue in position 1 to an albumin binding residue or a polyethylene glycol polymer, or c) adding a lysine residue in position 38 wherein said lysine residue is linked to an albumin binding residue or a polyethylene glycol polymer, optionally via a linker; wherein the amino acid numbering conforms with the amino acid numbering in SEQ ID No 1.

The present invention also provides pharmaceutical compositions comprising a derivative according to the present invention and the use of the derivatives according to the present invention for preparing medicaments for treating diseases.

DESCRIPTION OF THE INVENTION

The term "pharmaceutically acceptable" as used herein means suited for normal pharmaceutical applications, i.e. giving rise to no serious side-effects such as adverse events in patients etc.

The term "excipient" as used herein means the chemical compounds which are normally added to pharmaceutical compositions, e.g. buffers, tonicity agents, preservatives and the like.

The term "effective amount" as used herein means a dosage which is sufficient to be effective for the treatment of the patient compared with no treatment.

The term "pharmaceutical composition" as used herein means a product comprising an active derivative together with pharmaceutical excipients such as buffer, preservative, and optionally a tonicity modifier and/or a stabilizer. Thus, a pharmaceutical composition is also known in the art as a pharmaceutical formulation.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The invention relates in one aspect to a compound, which is a derivative of human amylin with SEQ ID No. 1 or an analog thereof, wherein a) an amino acid residue in position 2 to 37 has been substituted with a lysine residue or a cysteine residue, and wherein said lysine residue or cysteine residue is linked to an albumin binding residue or a polyethylene glycol polymer, or b) the lysine residue in position 1 is linked to an albumin binding residue or a polyethylene glycol polymer, or c) a lysine residue has been added in position 38 and wherein said lysine residue is linked to an albumin binding residue or a polyethylene glycol polymer optionally via a linker;
wherein the amino acid numbering conforms with the amino acid numbering in SEQ ID No 1.

The invention relates in one aspect to a compound, which is a derivative of human amylin with SEQ ID No 1 or an analog thereof, wherein a) an amino acid residue in position 2 to 37 has been substituted with a lysine residue or a cysteine residue and wherein said lysine residue or cysteine residue is linked to an albumin binding residue or a polyethylene glycol polymer, or b) the lysine residue in position 1 is linked to an albumin binding residue or a polyethylene glycol polymer, optionally via a linker;
wherein the amino acid numbering conforms with the amino acid numbering in SEQ ID No 1.

The invention relates in another aspect to a compound, which is a derivative of human amylin with SEQ ID No 1 or an analog thereof, wherein an amino acid residue in position 2 to 37 has been substituted with a lysine residue or a cysteine residue and wherein said lysine residue or cysteine residue is linked to an albumin binding residue or a polyethylene glycol polymer, optionally via a linker;
wherein the amino acid numbering conforms with the amino acid numbering in SEQ ID No 1.

The invention relates in another aspect to a compound, which is a derivative of human amylin of SEQ ID No 1, wherein a) an amino acid residue in position 2 to 37 of the human amylin has been substituted with a lysine residue or a cysteine residue and wherein said lysine residue or cysteine residue is linked to an albumin binding residue or a polyethylene glycol polymer, or b) the lysine residue in position 1 of the human amylin is linked to an albumin binding residue or a polyethylene glycol polymer, optionally via a linker;
wherein the amino acid numbering conforms with the amino acid numbering in SEQ ID No 1.

The invention relates in another aspect to a compound, which is a derivative of human amylin of SEQ ID No 1, wherein an amino acid residue in position 2 to 37 of human amylin has been substituted with a lysine residue or a cysteine residue, and wherein said lysine residue or cysteine residue is linked to an albumin binding residue or a polyethylene glycol polymer, optionally via a linker,
wherein the amino acid numbering conforms with the amino acid numbering in SEQ ID No 1.

The term "human amylin" as used herein refers to the peptide human amylin having the sequence as depicted in SEQ ID No 1. The term includes, but is not limited to, a human peptide hormone of 37 amino acids referred to as amylin, which is co-secreted with insulin from β-cells of the pancreas. Human amylin has the following amino acid sequence: Lys-Cys-Asn-Thr-Ala-Thr-Cys-Ala-Thr-Gln-Arg-Leu-Ala-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO:1). Thus, the structural formula is Lys-Cys-Asn-Thr-Ala-Thr-Cys-Ala-Thr-Gln-Arg-Leu-Ala-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr-NH$_2$ (SEQ ID NO:

1) as shown below with a disulfide bridge between the two Cys residues and a C-terminal amide group.

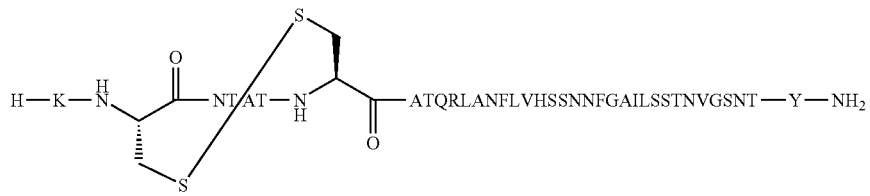

In the present text, the term "analog of human amylin" is used to designate a peptide wherein one or more amino acid residues of human amylin of SEQ ID No 1 independently have been substituted by other amino acid residues and/or wherein one or more amino acid residues of human amylin have been deleted and/or wherein one or more amino acid residues have been added to human amylin.

In one aspect of the invention, such addition or deletion of amino acid residues can take place at the N-terminal of the peptide and/or at the C-terminal of the peptide. An analog of human amylin has in one aspect preferably from 30 to 45 naturally occurring or non-naturally occurring amino acids, preferably from 35-40 naturally occurring or non-naturally occurring amino acids.

The term "derivative" is used in the present text to designate a peptide in which one or more of the amino acid residues of the peptide have been modified, e.g. by alkylation, acylation, ester formation, amide formation or by maleimide coupling.

The term "a derivative of human amylin or an analog thereof" or "an amylin derivative" is used in the present text to designate a derivative of human amylin or an analog thereof.

In a further aspect of the invention, an analog of human amylin has sufficient homology with human amylin such that it exhibits at least 70% in vivo activity compared to human amylin.

The compounds of the present invention may be capable of binding to or otherwise directly or indirectly interacting with an amylin receptor, or other receptor or receptors with which amylin itself may interact to elicit a biological response, e.g., reducing food intake. Compounds of the invention may bind an amylin receptor with an affinity better than 20 nM, 10 nM, or 5 nM, and more preferably with an affinity better than 2 nM, 1 nM, 0.5 nM, 0.2 nM or 0.10 nM.

In one embodiment according to the invention, the compounds of the present invention may retain at least about 25%, preferably about 30%, 40%, 50%, 60%, 70%, 80%, 90%, 95%, 98%, or 99% percent of the biological activity of amylin. In another embodiment, compounds of the invention exhibit improved biological activity. In a further embodiment, compounds of the present invention exhibit at least about 110%, 125%, 130%, 140%, 150%, 200%, or more of the biological activity of amylin.

The term "activity" refers in one embodiment to the ability to reduce appetite and/or increase satiety. In one aspect of the invention, activity is measured by the ability to reduce appetite as e.g. described in Pharmacological assays I and II under the heading "ASSAYS".

In one embodiment according to the invention, the compounds of the present invention may demonstrate an ability to reduce cumulative food intake more than 5% over administration of the vehicle, preferably more than 15%, more preferably more than 25%, even more preferably more than 35% or 40% most preferably more than 50% over the vehicle.

The term "activity" refers in another embodiment to the ability to delay gastric emptying in an animal model. The term "activity" refers in another embodiment to the ability to inhibit release of glucagon in an animal model.

The term "time of action" refers in the present context to the time span where a pharmacological effect such as reduced food intake is measurable.

In one embodiment according to the invention, the amylin derivative is less likely to fibrillate in vivo and/or ex-vivo compared to human amylin. The tendency of fibrillation may e.g. be estimated in a Thioflavin T test as described below under the definition of the term "physical stability".

In one embodiment according to the invention, the amylin derivative has a protracted pharmaco-kinetic profile compared to pramlintide as measured by standard procedures such as ELISA known to people skilled in the art. In another embodiment of the invention, the amylin derivative has a plasma t½ of at least 1 hour. In another embodiment, of the invention the plasma t½ is at least 1.5 hour. In another embodiment of the invention, the amylin derivative has a plasma t½ of at least 2 hours. In another embodiment of the invention, the amylin derivative has a plasma t½ of at least 4 hours. In another embodiment of the invention, the amylin derivative has a plasma t½ of at least 6 hours. In another embodiment of the invention, the amylin derivative has a plasma t½ of at least 8 hours. In another embodiment of the invention, the amylin derivative has a plasma t½ of at least 12 hours. In another embodiment of the invention, the amylin derivative has a plasma t½ of at least 16 hours. In another embodiment of the invention, the amylin derivative has a plasma t/2 of at least 24 hours. In one embodiment of the invention, the amylin derivative has a plasma t/2 of at least 48 hours. In one embodiment of the invention, the amylin derivative has a plasma t/2 of at least 96 hours.

In another further aspect of the invention, an analog of human amylin has the amino acid sequence of human amylin modified so that from one, two, three, four, five, or six or seven or eight amino acids differ from the amino acid in the corresponding position of human amylin. In another further aspect of the invention, an analog comprises less than 8 modifications (substitutions, deletions, additions) relative to human amylin. In another further aspect of the invention, an analog comprises less than 7 modifications (substitutions, deletions, additions) relative to human amylin. In another further aspect of the invention, an analog comprises less than 6 modifications (substitutions, deletions, additions) relative to human amylin. In another further aspect of the invention, an analog comprises less than 5 modifications (substitutions, deletions, additions) relative to human amylin. In another further aspect of the invention, an analog comprises less than 4 modifications (substitutions, deletions, additions) relative to human amylin. In another further aspect of the invention, an analog comprises less than 3 modifications (substitutions, deletions, additions) relative to human amylin. In another further aspect of the invention, an analog comprises less than 2 modifications (substitutions, deletions, additions) relative to human amylin. In another further aspect of the invention, an analog comprises only a single modification (substitutions, deletions, additions) relative to human amylin.

In one aspect of the invention, the modification(s) are substitution(s). In one aspect of the invention, the modification(s) are deletion(s). In one aspect of the invention, the modification(s) are addition(s).

In one aspect of the invention, the amino acid residue in position 2, 3, 4, 5, or 6 is substituted with a lysine residue or a cysteine residue and said lysine residue or cysteine residue is linked to an albumin binding residue or a polyethylene glycol polymer, optionally via a linker.

In one aspect of the invention, the amino acid residue in position 23, 24, 25, 26, 27 or 28 is substituted with a lysine residue or a cysteine residue and said lysine residue or cysteine residue is linked to an albumin binding residue or a polyethylene glycol polymer, optionally via a linker.

In one aspect of the invention, the amino acid residue in position 32, 33, 34, 35, 36 or 37 is substituted with a lysine residue or a cysteine residue and said lysine residue or cysteine residue is linked to an albumin binding residue or a polyethylene glycol polymer, optionally via a linker.

In a further aspect of the invention, one, two or all of the amino acid residue(s) in position 25, 28 and 29 is substituted with a proline residue. In a further aspect of the invention, the amino acid residue in position 25 is substituted with a proline residue. In a further aspect of the invention, the amino acid residue in position 28 is substituted with a proline residue. In a further aspect of the invention, the amino acid residue in position 29 is substituted with a proline residue. In a further aspect of the invention, the amino acid residue in position 18 is substituted with an arginine residue. In a further aspect of the invention, the amino acid residue in position 23 is substituted with a leucine residue. In a further aspect of the invention, the amino acid residue in position 26 is substituted with a valine residue.

The invention relates in another aspect to a compound, which is a derivative of human amylin with SEQ ID No. 1 or an analog thereof, wherein
an amino acid residue in position 2 to 37 has been substituted with a lysine residue and wherein said lysine residue is linked to an albumin binding residue or a polyethylene glycol polymer
optionally via a linker;
wherein the amino acid numbering conforms with the amino acid numbering in SEQ ID No 1.

The invention relates in another aspect to a compound which is a derivative of human amylin with SEQ ID No. 1 or an analog thereof, wherein
the lysine residue in position 1 is linked to an albumin binding residue or a polyethylene glycol polymer,
optionally via a linker;
wherein the amino acid numbering conforms with the amino acid numbering in SEQ ID No 1.

The invention relates in another aspect to a compound which is a derivative of human amylin with SEQ ID No. 1 or an analog thereof, wherein
a lysine residue has been added in position 38 and wherein said lysine residue is linked to an albumin binding residue or a polyethylene glycol polymer
optionally via a linker;
wherein the amino acid numbering conforms with the amino acid numbering in SEQ ID No 1.

The invention relates in another aspect to a derivative of human amylin with SEQ ID No. 1.

The invention relates in another aspect to a derivative of a human amylin analog.

The invention relates in another aspect to a derivative, wherein the amino acid residue in position 2, 3, 4, 5, or 6 is substituted with a lysine residue and wherein said lysine residue is linked to an albumin binding residue or a polyethylene glycol polymer, optionally via a linker.

The invention relates in another aspect to a derivative, wherein the amino acid residue in position 23, 24, 25, 26, 27 or 28 is substituted with a lysine residue and wherein said lysine residue is linked to an albumin binding residue or a polyethylene glycol polymer, optionally via a linker.

The invention relates in another aspect to a derivative, wherein the amino acid residue in position 32, 33, 34, 35, 36 or 37 is substituted with a lysine residue and wherein said lysine residue is linked to an albumin binding residue or a polyethylene glycol polymer, optionally via a linker.

The invention relates in another aspect to a derivative, wherein the amino acid residue in position 1 is substituted with a lysine residue and wherein said lysine residue is linked to an albumin binding residue or a polyethylene glycol polymer, optionally via a linker.

The invention relates in another aspect to a derivative, wherein the albumin binding residue or the polyethylene glycol polymer, optionally via a linker is linked via the ε-amino group of the lysine residue.

The invention relates in another aspect to a derivative, wherein the albumin binding residue or the polyethylene glycol polymer, optionally via a linker is linked via the alpha-amino group of the lysine residue.

The invention relates in another aspect to a derivative, wherein the amino acid residue in any one of position 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 is substituted with a lysine residue and wherein said lysine residue is linked to an albumin binding residue or a polyethylene glycol polymer, optionally via a linker.

The invention relates in another aspect to a derivative, wherein the amino acid residue in any one of position 1, 10, 11, 14, 15, 16, 17, 18, 21, 22, 25, 28, 29, 31, 35 or 38 is substituted with a lysine residue and wherein said lysine residue is linked to an albumin binding residue or a polyethylene glycol polymer, optionally via a linker.

The invention relates in another aspect to a derivative, wherein the amino acid residue in any one of position 1, 11, 17, 21, 22, 25, 28, 29 or 31 is substituted with a lysine residue and wherein said lysine residue is linked to an albumin binding residue or a polyethylene glycol polymer, optionally via a linker.

The invention relates in another aspect to a derivative, wherein the amino acid residue in position 1, 11, 17, 21, 22, 25, 28, 29 or 31 is substituted with a lysine residue and wherein said lysine residue is linked to an albumin binding residue, optionally via a linker.

The invention relates in another aspect to a derivative, wherein the amino acid residue in any one of position 1, 11, 17, 21, 22 or 31 is substituted with a lysine residue and wherein said lysine residue is linked to an albumin binding residue or a polyethylene glycol polymer, optionally via a linker.

The invention relates in another aspect to a derivative, wherein the amino acid residue in position 21 is substituted with a lysine residue and wherein said lysine residue is linked to an albumin binding residue or a polyethylene glycol polymer, optionally via a linker.

The invention relates in another aspect to a derivative, wherein the amino acid residue in position 22 is substituted with a lysine residue and wherein said lysine residue is linked to an albumin binding residue or a polyethylene glycol polymer, optionally via a linker.

The invention relates in another aspect to a derivative, wherein the amino acid residue in position 17 is substituted with a lysine residue and wherein said lysine residue is linked to an albumin binding residue or a polyethylene glycol polymer, optionally via a linker.

The invention relates in another aspect a derivative, wherein the amino acid residue in position 31 is substituted with a lysine residue and wherein said lysine residue is linked to an albumin binding residue or a polyethylene glycol polymer, optionally via a linker.

The invention relates in another aspect to a derivative, wherein the amino acid residue in position 11 is substituted with a lysine residue and wherein said lysine residue is linked to an albumin binding residue or a polyethylene glycol polymer, optionally via a linker.

The invention relates in another aspect to a derivative, wherein the amino acid residue in position 28 is substituted with a lysine residue and wherein said lysine residue is linked to an albumin binding residue or a polyethylene glycol polymer, optionally via a linker.

The invention relates in another aspect to a derivative, wherein the amino acid residue in position 25 is substituted with a lysine residue and wherein said lysine residue is linked to an albumin binding residue or a polyethylene glycol polymer, optionally via a linker.

The invention relates in another aspect to a derivative, wherein the amino acid residue in position 29 is substituted with a lysine residue and wherein said lysine residue is linked to an albumin binding residue or a polyethylene glycol polymer, optionally via a linker.

The invention relates in another aspect to a derivative, wherein the lysine residue is linked to an albumin binding residue via a linker.

In another aspect of the invention, the derivative has from 1-6 amino acid substitutions compared to human amylin.

In another aspect of the invention, the derivative has from 1-4 amino acid substitutions compared to human amylin.

In a further aspect of the invention, -FGAILSS- (SEQ ID No. 2) in position 23 to 29 is changed to -FGPILPP- (SEQ ID No. 3).

In a further aspect of the invention, -FGAILSS- (SEQ ID No. 2) in position 23 to 29 is changed to -FGEILSS- (SEQ ID No. 4).

In a further aspect of the invention, -FGAILSS- (SEQ ID No. 2) in position 23 to 29 is changed to -FGDILSS- (SEQ ID No. 5).

The term "linked to" as used herein means chemically connected via a covalent bond. For example a lysine residue or cysteine residue is linked to an albumin binding residue via a chemical bond. Such a chemical bond can as an example be obtained by derivatisation of an epsilon amino group of lysine by acylation with an active ester of an albumin binding residue such as a long fatty acid.

Other examples of connecting two chemical moieties as used in the present invention includes but is not limited to alkylation, ester formation, amide formation or maleimide coupling.

The term "albumin binding residue" as used herein means in one aspect of the invention a residue which binds non-covalently to human serum albumin. The albumin binding residue attached to the therapeutic polypeptide typically has an affinity (binding constant) below 10 µM to human serum albumin and preferably below 1 µM. A range of albumin binding residues are known among linear and branched lipohophillic moieties containing 4-40 carbon atoms, compounds with a cyclopentanophenanthrene skeleton, peptides having 10-30 amino acid residues etc.

Albumin binding affinity may be determined by several methods known within the art. In one method the compound to be measured is radiolabeled with e.g. $^{125}I$ or $^{3}H$ and incubated with immobilized albumin (Kurtzhals et. al., Biochem. J., 312, 725-731 (1995)). The binding of the compound relative to a standard is calculated. In another method a related compound is radiolabeled and its binding to albumin immobilized on e.g. SPA beads is competed by a dilution series of the compound to be measured. The EC50 value for the competition is a measure of the affinity of the compound. In a third method, the receptor affinity or potency of a compound is measured at different concentrations of albumin, and the shift in relative affinity or potency of the compound as a function of albumin concentration reflects its affinity for albumin.

The term "$C_{1-6}$-alkyl" as used herein means a saturated, branched, straight or cyclic hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl, cyclohexane and the like.

The term "linker" as used herein means a spacer (the two terms spacer and linker is used interchangeably in the present specification) that separates a peptide and an albumin binding residue or a polyethylene glycol polymer.

The term "hydrophilic linker" as used herein means a spacer that separates a peptide and an albumin binding residue with a chemical moiety which comprises at least 5 heavy atoms where 30-50% of these are either N or O.

In one aspect of the invention, the linker comprises an unbranched alkane α,ω-dicarboxylic acid group having from 1 to 7 methylene groups, preferably two methylene groups which linker forms a bridge between an amino group of the peptide and an amino group of the albumin binding residue or a polyethylene glycol polymer.

In another aspect of the invention, the linker comprises one or more alkylene glycol units, such as 1 to 5 alkylene glycol units. The alkylene glycol units are in a further aspect ethylene glycol, propylene glycol or butylene glycol but can also be higher alkylene glycols.

In another aspect of the invention, the linker is a hydrophilic linker selected from

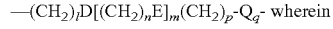
—$(CH_2)_l D[(CH_2)_n E]_m (CH_2)_p$-$Q_q$- wherein l, m and n independently are 1-20 and p is 0-10,
Q is —Z—$(CH_2)_l D[(CH_2)_n G]_m (CH_2)_p$—,
q is an integer in the range from 0 to 5,
each D, E, and G are independently selected from —O—, —$NR^3$—, —$N(COR^4)$—, —$PR^5(O)$—, and —$P(OR^6)$(O)—, wherein $R^3$, $R^4$, $R^5$, and $R^6$ independently represent hydrogen or $C_{1-6}$-alkyl,
Z is selected from —C(O)NH—, —C(O)NHCH$_2$—, —OC(O)NH—, —C(O)NHCH$_2$CH$_2$—, —C(O)CH$_2$—, —C(O)CH=CH—, —$(CH_2)_s$—, —C(O)—, —C(O)O— or —NHC(O)—, wherein s is 0 or 1.

In another aspect of the invention, the linker is a hydrophilic linker as defined above wherein l is 1 or 2, n and m are independently 1-10 and p is 0-10.

In another aspect of the invention, the linker is a hydrophilic linker as defined above wherein D is —O—.

In another aspect of the invention, the linker is a hydrophilic linker as defined above wherein E is —O—.

In yet another aspect of the invention, the hydrophilic linker is

—CH$_2$O[(CH$_2$)$_2$O]$_m$(CH$_2$)$_p$Q$_q$-, wherein m is 1-10, p is 1-3, and Q is —Z—CH$_2$O[(CH$_2$)$_2$O]$_m$(CH$_2$)$_p$— wherein Z is as defined above.

In another aspect of the invention, the linker is a hydrophilic linker as defined above wherein q is 1.

In another aspect of the invention, the linker is a hydrophilic linker as defined above wherein G is —O—.

In another aspect of the invention, the linker is a hydrophilic linker as defined above wherein Z is selected from the group consisting of —C(O)NH—, —C(O)NHCH$_2$—, and —OC(O)NH—.

In another aspect of the invention, the linker is a hydrophilic linker as defined above wherein q is 0.

In another aspect of the invention, the linker is a hydrophilic linker as defined above wherein L is 2.

In another aspect of the invention, the linker is a hydrophilic linker as defined above wherein n is 2.

In one aspect of this invention a "hydrophilic linker" B is used that separates a peptide and an albumin binding residue with a chemical moiety.

In one aspect of this invention, the hydrophilic linker B is

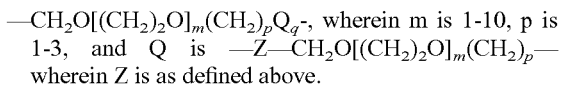

wherein l, m, n, and p independently are 1-5, and q is 0-5.

In yet another aspect of this invention, the hydrophilic linker B is

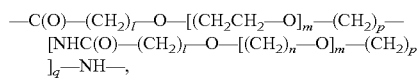

wherein q is 0-5.

In yet another aspect of this invention, the hydrophilic linker B is

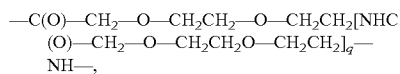

In yet another aspect of the invention, the hydrophilic linker B is —[CH$_2$CH$_2$O]$_{m+1}$(CH$_2$)$_p$Q$_q$- wherein m and p independently is 0-10, q is 0-5 and Q is —Z—(CH$_2$)$_l$D[(CH$_2$)$_n$G]$_m$(CH$_2$)$_p$— as defined above.

In yet another aspect of the invention, the hydrophilic linker B is

wherein l, m, n, and p independently are 1-5, and q is 0-5.

In a further aspect of the invention, the linker comprises an amino acid residue except Cys, or a dipeptide such as Gly-Lys. In the present text, the expression "a dipeptide such as Gly-Lys" is used to designate a dipeptide wherein the C-terminal amino acid residue is Lys, H is or Trp, preferably Lys, and wherein the N-terminal amino acid residue is selected from the group comprising Ala, Arg, Asp, Asn, Gly, Glu, Gln, Ile, Leu, Val, Phe and Pro.

Suitable PEG polymers are typically commercially available or may be made by techniques well-known to those skilled in the art.

In one aspect of the invention, the PEG polymer has a molecular weight of greater than 700D, in a further aspect a molecular weight greater than 5 kD, in yet a further aspect greater than 10 kD, and in a even further aspect greater that 20 kD. The PEG polymer may be linear or branched. In cases where the PEG polymer is greater than 20 KDa, the PEG polymer is preferable having a branched structure, such as for example, a 43 kD branched PEG-peptide (Shearwater 2001 catalog #2D3XOT01, mPEG2-MAL).

The attachment of a PEG on an intact peptide can be accomplished by attaching the PEG on the opposite side of the peptide surface that interacts with the receptor.

In one aspect of the invention, the attachment of PEG will occur on the amino acid residue in position 2, 3, 4, 5, or 6 of human amylin or an analog thereof which is substituted with a lysine residue or a cysteine, optionally via a linker. In a further aspect of the invention, the attachment of PEG will occur on the amino acid residue in position 23, 24, 25, 26, 27 or 28 of human amylin or an analog thereof which is substituted with a lysine residue or a cysteine, optionally via a linker. In yet a further aspect of the invention, the attachment of PEG will occur on the amino acid residue in position 32, 33, 34, 35, 36, or 37 of human amylin or an analog thereof which is substituted with a lysine residue or a cysteine, optionally via a linker.

There are several strategies for coupling PEG to peptides (see, e.g. Veronese, Biomaterials 22:405-417, 2001), all of which are incorporated herein by reference in their entirety. Those skilled in the art, will therefore be able to utilize well-known techniques for linking the PEG polymer to human amylin or the amylin analogs described herein.

Briefly, cysteine PEGylation is one method for site-specific PEGylation, and can be accomplished by introducing a unique cysteine mutation at one of the specific positions on human amylin or the amylin analog and then reacting the resulting peptide with a cysteine-specific PEGylation reagent, such as PEG-maleimide. It may be necessary to mutate the peptide in order to allow for site-specific PEGylation. For example, if the peptide contains cysteine residues, these will need to be substituted with conservative amino acids in order to ensure site-specific PEGylation.

In addition, rigid linkers, including but not limited to "GGS", "GGSGGS", and "PPPS" may be added to the C-terminus, but before the site of PEG attachment (i.e. a unique cysteine residue).

In one aspect of the invention, the albumin binding residue is a lipophilic residue. In a further aspect, the lipophilic residue is attached to a lysine residue optionally via a linker by conjugation chemistry such as by alkylation, acylation, ester formation, or amide formation or to a cysteine residue by maleimide coupling.

In a further aspect of the invention, the albumin binding residue is negatively charged at physiological pH. In another aspect of the invention, the albumin binding residue comprises a group which can be negatively charged. One preferred group which can be negatively charged is a carboxylic acid group.

In a further aspect of the invention, the albumin binding residue binds non-covalently to albumin. In another aspect of the invention, the albumin binding residue has a binding affinity towards human serum albumin better than about 10 μM or better than about 1 μM.

In yet another aspect of the invention, the albumin binding residue is selected from the group consisting of a straight chain alkyl group, a branched alkyl group, a group which has an ω-carboxylic acid group, and a partially or completely hydrogenated cyclopentanophenanthrene skeleton.

In a further aspect of the invention, the albumin binding residue is a cibacronyl residue.

In a further aspect of the invention, the albumin binding residue has from 6 to 40 carbon atoms, from 8 to 26 carbon atoms or from 8 to 20 carbon atoms.

In a further aspect of the invention, the albumin binding residue is an acyl group selected from the group comprising $CH_3(CH_2)_rCO-$, wherein r is an integer from 4 to 38, preferably an integer from 4 to 24, more preferred selected from the group comprising $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$.

In another aspect of the invention, the albumin binding residue is an acyl group of a straight-chain or branched alkane α,ω-dicarboxylic acid.

In another aspect of the invention, the albumin binding residue is an acyl group selected from the group comprising $HOOC(CH_2)_sCO-$, wherein s is an integer from 4 to 38, preferably an integer from 4 to 24, more preferred selected from the group comprising $HOOC(CH_2)_{14}CO-$, $HOOC(CH_2)_{16}CO-$, $HOOC(CH_2)_{18}CO-$, $HOOC(CH_2)_{20}CO-$ and $HOOC(CH_2)_{22}CO-$.

In another aspect of the invention, the albumin binding residue is a group of the formula $CH_3(CH_2)_vCO-NHCH(COOH)(CH_2)_2CO-$, wherein v is an integer from 10 to 24.

In another aspect of the invention, the albumin binding residue is a group of the formula $CH_3(CH_2)_wCO-NHCH((CH_2)_2COOH)CO-$, wherein w is an integer from 8 to 24.

In another aspect of the invention, the albumin binding residue is a group of the formula $COOH(CH_2)_xCO-$ wherein x is an integer from 8 to 24.

In another aspect of the invention, the albumin binding residue is a group of the formula $-NHCH(COOH)(CH_2)_4NH-CO(CH_2)_yCH_3$, wherein y is an integer from 8 to 18.

In one aspect of this invention, the combined albumin binding residue and linker is

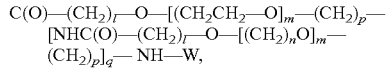

wherein l, m, n, and p independently are 1-5, and q is 0-5 and W is selected from the group consisting of $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$, $CH_3(CH_2)_{22}CO-$, $HOOC(CH_2)_{14}CO-$, $HOOC(CH_2)_{16}CO-$, $HOOC(CH_2)_{18}CO-$, $HOOC(CH_2)_{20}CO-$ and $HOOC(CH_2)_{22}CO-$.

In one aspect of this invention, the combined albumin binding residue and linker is

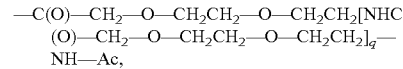

wherein q is 0-5 and wherein Ac is acetyl.

In another aspect of this invention, the combined albumin binding residue and linker is a group of the formula

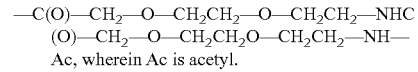

Ac, wherein Ac is acetyl.

In another aspect of this invention, the combined albumin binding residue and linker is

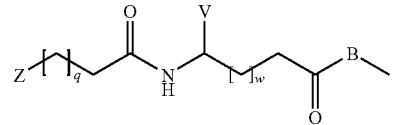

wherein B is defined as described above, and Z, V, q and w is defined as below.

In another aspect of this invention, the combined albumin binding residue and linker is

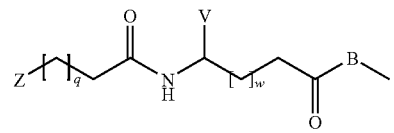

wherein Z is $CH_3$ or COOH, V is H or COOH, q is 7 to 21, w is 0 to 5, and k is 0 to 5 and B is $-C(O)-(CH_2)_l-O-[(CH_2CH_2-O]_m-(CH_2)_p-[NHC(O)-(CH_2)_l-O-[(CH_2)_n-O]_m-(CH_2)_p]_q-NH-$, wherein l, m, n, and p independently are 1-5, and q is 0-5.

In another aspect of this invention, the combined albumin binding residue and linker is

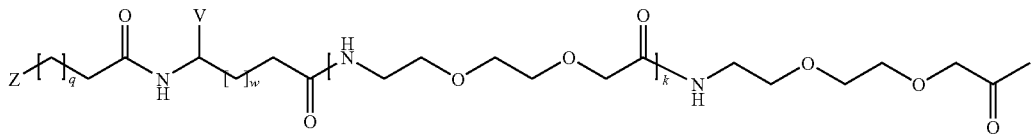

wherein Z is $CH_3$ or COOH, V is H or COOH, q is 7 to 21, w is 0 to 5, and k is 0 to 5. In another aspect of this invention, Z is $CH_3$ and V is COOH. In another aspect of this invention V is H and Z is COOH. In another aspect of this invention, V is H and Z is $CH_3$. In another aspect of this invention, V and Z are both COOH. In a preferred aspect of this invention, q is 13 to 19, and more preferable q is 13 to 15. In a preferred aspect of this invention, k is 1 to 4, and more preferable 1 to 2. In a preferred aspect of this invention, w is 1 to 4, and more preferable 1 to 2.

In another aspect of this invention, the combined albumin binding residue and linker is

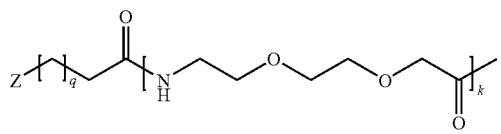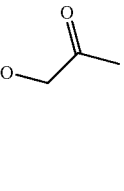

wherein Z is $CH_3$ or COOH, q is 7 to 21, and k is 0 to 5. In another aspect of this invention, Z is $CH_3$. In another aspect of this invention, Z is COOH. In a preferred aspect of this invention, q is 13 to 19, and more preferable q is 13, 14 or 15. In a preferred aspect of this invention, k is 1 to 4, and more preferable 1 or 2.

In another aspect of the invention, the albumin binding residue is a peptide, such as a peptide comprising less than 40 amino acid residues. A number of small peptides which are albumin binding residues as well as a method for their identification is found in J. Biol. Chem. 277, 38 (2002) 35035-35043.

In another aspect of the invention, the albumin binding residue optionally via a linker is attached via the ε-amino group of a lysine residue.

In another aspect of the invention, the albumin binding residue optionally via a linker is attached via a cysteine residue.

In a further aspect, the present invention relates to a amylin derivative wherein a lipophilic residue is attached to the parent peptide by means of a linker which is an amino acid residue except Cys, or is a dipeptide such as Gly-Lys, and wherein a carboxyl group of the parent peptide forms an amide bond with an amino group of a Lys residue or a dipeptide containing a Lys residue, and the other amino group of the Lys residue or a dipeptide containing a Lys residue forms an amide bond with a carboxyl group of the lipophilic residue.

In a further aspect, the present invention relates to a amylin derivative wherein a lipophilic residue is attached to the parent peptide by means of a linker which is an amino acid residue except Cys, or is a dipeptide such as Gly-Lys, and wherein an amino group of the parent peptide forms an amide bond with a carboxylic group of the amino acid residue or dipeptide linker, and an amino group of the amino acid residue or dipeptide linker forms an amide bond with a carboxyl group of the lipophilic residue.

In a further aspect, the present invention relates to a amylin derivative wherein a lipophilic residue is attached to the parent peptide by means of a linker which is an amino acid residue except Cys, or is a dipeptide such as Gly-Lys, and wherein a carboxyl group of the parent peptide forms an amide bond with an amino group of the amino acid residue linker or dipeptide linker, and the carboxyl group of the amino acid residue linker or dipeptide linker forms an amide bond with an amino group of the lipophilic residue.

In a further aspect, the present invention relates to a amylin derivative wherein a lipophilic residue is attached to the parent peptide by means of a linker which is an amino acid residue except Cys, or is a dipeptide such as Gly-Lys, and wherein a carboxyl group of the parent peptide forms an amide bond with an amino group of a linker which is Asp or Glu, or a dipeptide linker containing an Asp or Glu residue, and a carboxyl group of the linker forms an amide bond with an amino group of the lipophilic residue.

In one aspect of the invention, the C-terminal of the amylin derivative may be terminated as either an acid or amide. In a preferred aspect, the C-terminal of the amylin derivative is an amide.

In one aspect of the invention, the amino acid sequence of the amylin derivative is selected from the group consisting of:

```
                                  (SEQ ID No. 24)
KCNTATCATQRLANFLVHSSNNFGPILPPTNVGSNTY, (SEQ ID No. 6)
KCNTATCATQRLANFLVHSSNNFGPILPPTKVGSNTY, (SEQ ID No. 7)
KCNTATCATQRLANFLVHSSNNFGPILPPTNVGSNTYK, (SEQ ID No. 8)
KCNTATCATQRLANFLVHSSNNFGPILKPTNVGSNTY, (SEQ ID No. 9)
KCNTATCATQKLANFLVHSSNNFGPILPPTNVGSNTY, (SEQ ID No. 10)
KCNTATCATQRLANFLVHSSKNFGPILPPTNVGSNTY, (SEQ ID No. 11)
KCNTATCATQRLANFLVHSSNKFGPILPPTNVGSNTY, (SEQ ID No. 12)
KCNTATCATQRLANFKVHSSNNFGPILPPTNVGSNTY, (SEQ ID No. 13)
KCNTATCATQRLANFLKHSSNNFGPILPPTNVGSNTY, (SEQ ID No. 14)
KCNTATCATQRLAKFLVHSSNNFGPILPPTNVGSNTY, (SEQ ID No. 15)
KCNTATCATQRLANKLVHSSNNFGPILPPTNVGSNTY, (SEQ ID No. 16)
KCNTATCATKRLANFLVHSSNNFGPILPPTNVGSNTY, (SEQ ID No. 17)
KCNTATCATQRLANFLVHSSNNFGPILPPTNVGSKTY, (SEQ ID No. 18)
KCNTATCATQRLANFLVRSSNNLGPVLPPTNVGSNTYK, (SEQ ID No. 19)
KCNTATCATQRLANFLVKSSNNFGPILPPTNVGSNTY, (SEQ ID No. 20)
KCNTATCATQRLANFLVHSSNNFGPILPKTNVGSNTY, (SEQ ID No. 21)
KCNTATCATQRLANFLVKSSNNLGPVLPPTNVGSNTY,
```

```
                                                     (SEQ ID No. 22)
KCNTATCATQKLANFLVRSSNNLGPVLPPTNVGSNTY,
and (SEQ ID No. 23)
KCNTATCATQRLANFLVHSSNNFGKILPPTNVGSNTY.
``` wherein at least one of the lysine residue(s) is linked to an albumin binding residue or a polyethylene glycol polymer, optionally via a linker.

In a further aspect, only one lysine residue in an amylin derivative is linked to an albumin binding residue or a polyethylene glycol polymer, optionally via a linker.

In a preferred aspect, the C-terminal of the amylin derivatives having any one of the amino acid sequences of SEQ ID No 6 to 24 is an amide.

In a further aspect of the invention, the albumin binding residue combined with a linker is selected from the group consisting of:

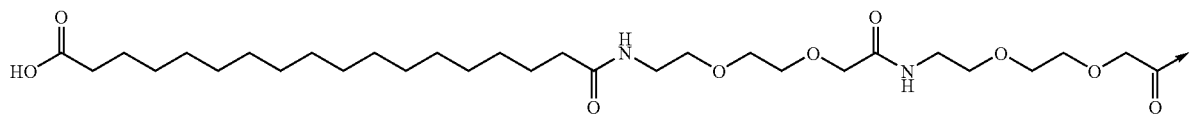

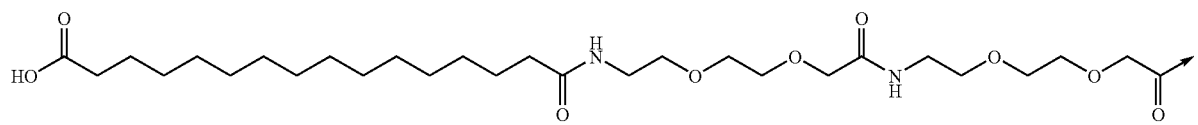

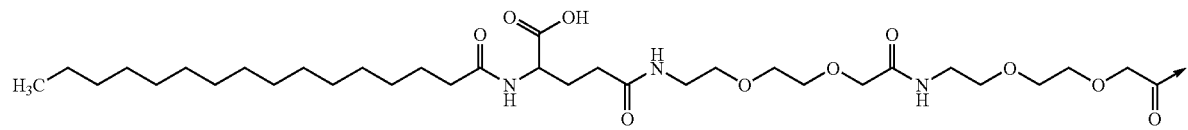

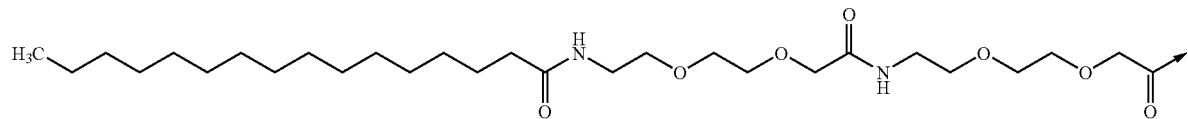

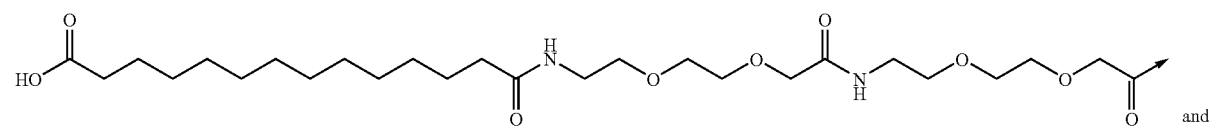

and

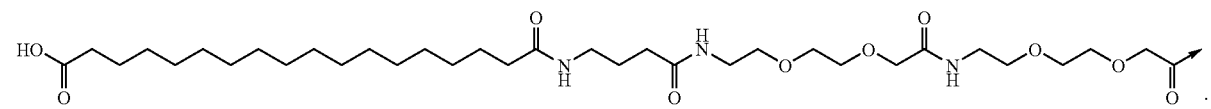

.

In one aspect of the invention, the amylin derivative is selected from the group consisting of
KCNTATCATQRLANFLVHSSNNFG-PILPPTNVGSNTY (SEQ ID No 24), wherein the lysine residue in position 1 is linked to an albumin binding residue combined with a linker with the following formula:

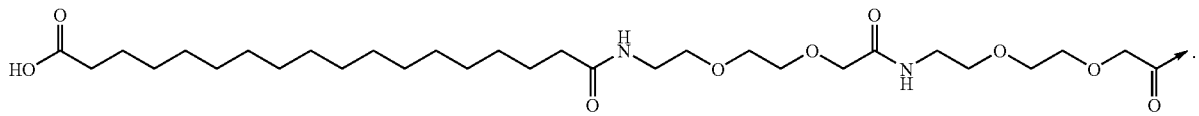

KCNTATCATQRLANFLVHSSNNFG-PILPPTKVGSNTY (SEQ ID No. 6), wherein the lysine residue in position 31 is linked to an albumin binding residue combined with a linker selected from the group consisting of

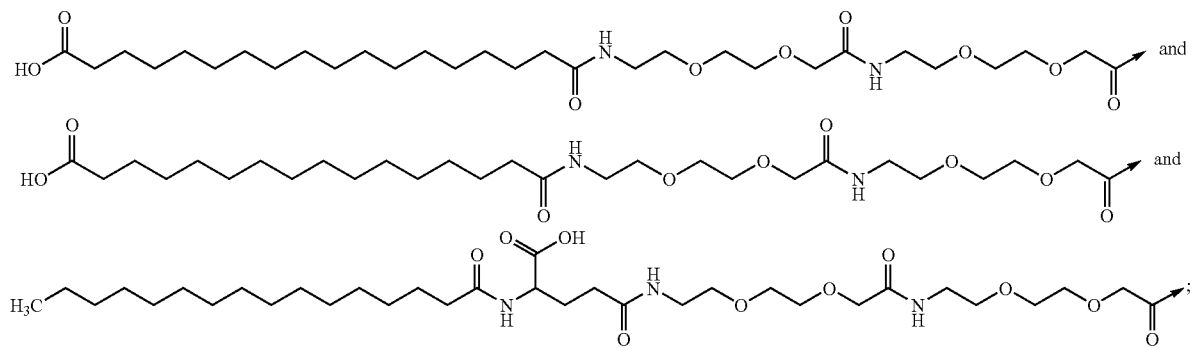

KCNTATCATQRLANFLVHSSNNFG-PILPPTNVGSNTYK (SEQ ID No. 7), wherein the lysine residue in position 38 is linked to an albumin binding residue combined with a linker selected from the group consisting of

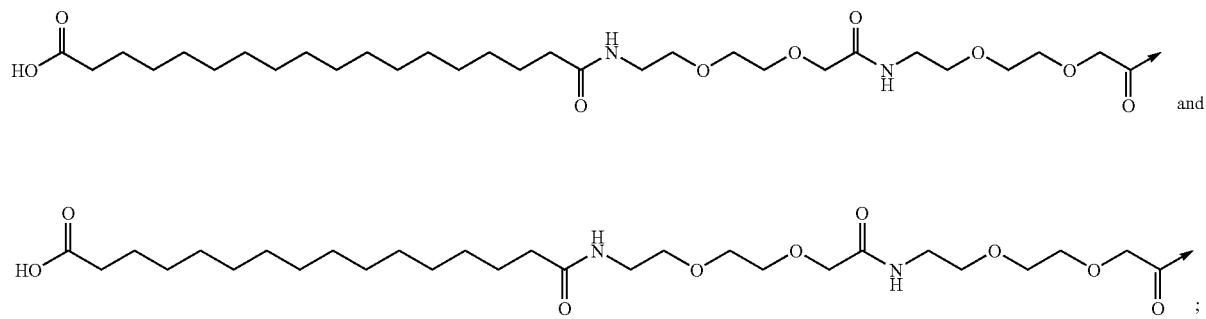

KCNTATCATQRLANFLVHSSNNFG-PILKPTNVGSNTY (SEQ ID No. 8), wherein the lysine residue in position 28 is linked to an albumin binding residue combined with a linker selected from the group consisting of

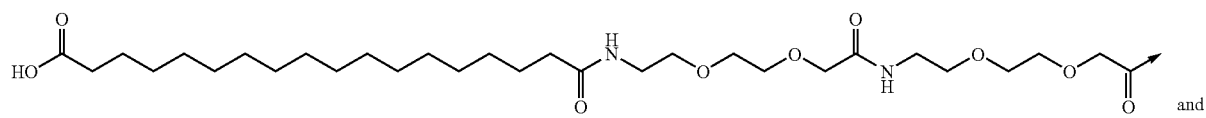

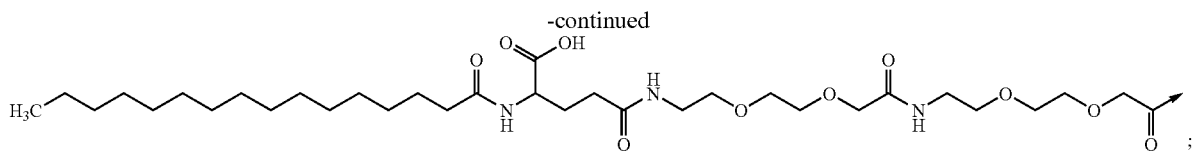
;

KCNTATCATQKLANFLVHSSNNFG-PILPPTNVGSNTY (SEQ ID No. 9), wherein the lysine residue in position 11 is linked to an albumin binding residue combined with a linker selected from the group consisting of

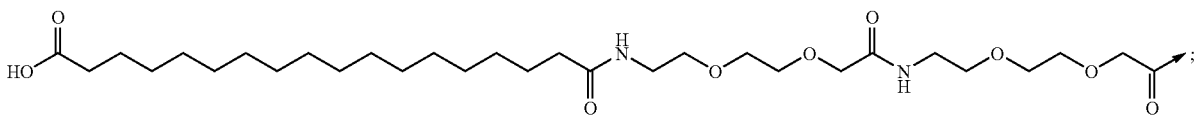
;

KCNTATCATQRLANFLVHSSKNFG-PILPPTNVGSNTY (SEQ ID No. 10), wherein the lysine residue in position 21 is linked to an albumin binding residue combined with a linker selected from the group consisting of

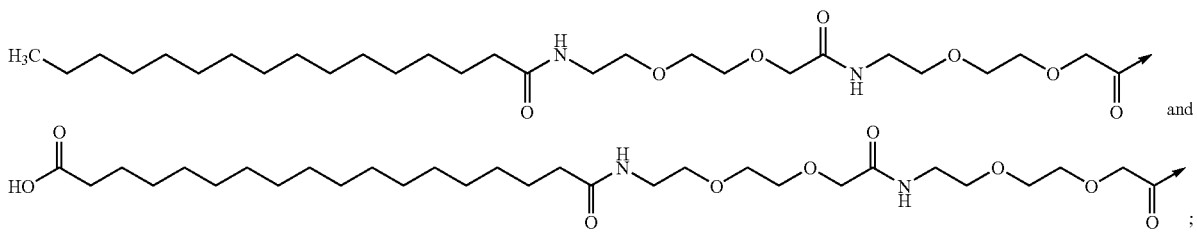

KCNTATCATQRLANFLVHSSNKFG-PILPPTNVGSNTY (SEQ ID No. 11), wherein the lysine residue in position 22 is linked to an albumin binding residue combined with a linker selected from the group consisting of

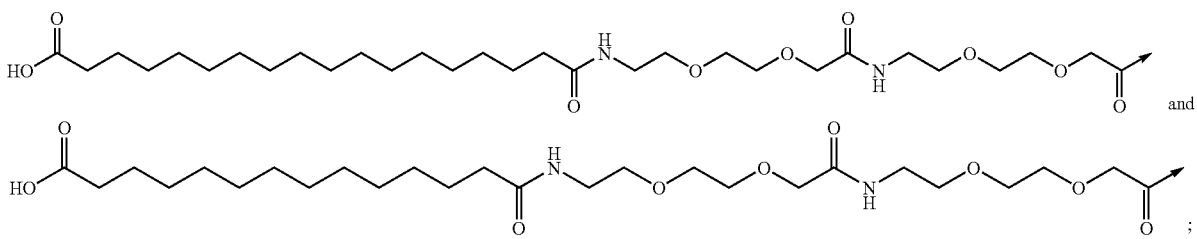

KCNTATCATQRLANFKVHSSNNFG-PILPPTNVGSNTY (SEQ ID No. 12), wherein the lysine residue in position 16 is linked to an albumin binding residue combined with a linker selected from the group consisting of

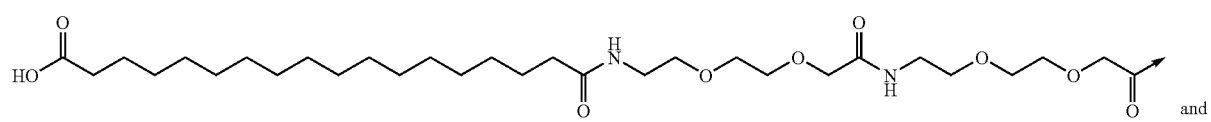

-continued

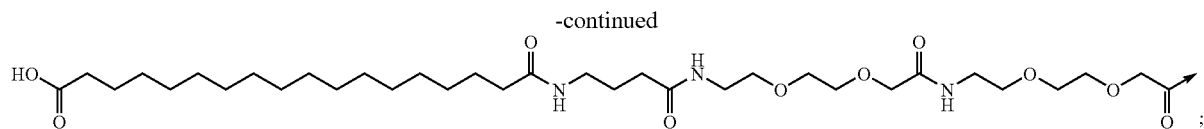

KCNTATCATQRLANFLKHSSNNFG-PILPPTNVGSNTY (SEQ ID No. 13), wherein the lysine residue in position 17 is linked to an albumin binding residue combined with a linker selected from the group consisting of

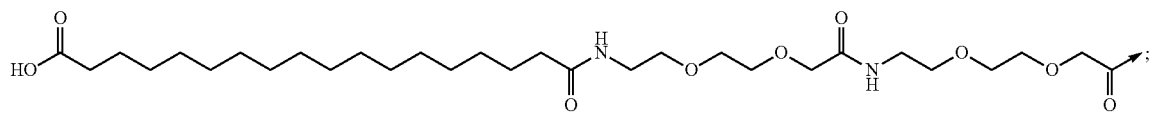

KCNTATCATQRLAKFLVHSSNNFG-PILPPTNVGSNTY (SEQ ID No. 14), wherein the lysine residue in position 14 is linked to an albumin binding residue via a linker selected from the group consisting of

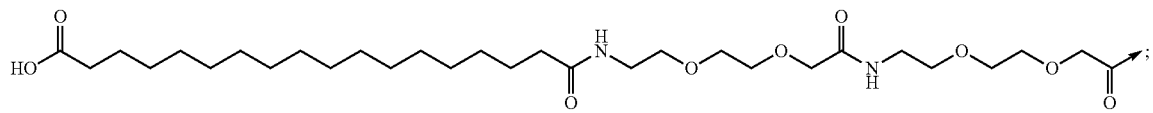

KCNTATCATQRLANKLVHSSNNFG-PILPPTNVGSNTY (SEQ ID No. 15), wherein the lysine residue in position 15 is linked to an albumin binding residue combined with a linker selected from the group consisting of

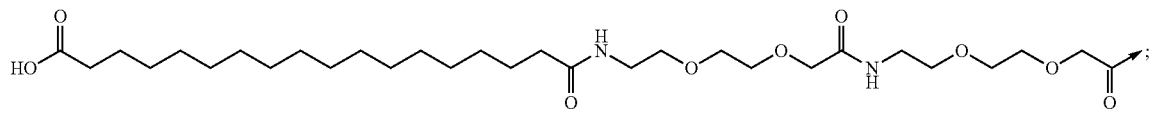

KCNTATCATKRLANFLVHSSNNFG-PILPPTNVGSNTY (SEQ ID No. 16), wherein the lysine residue in position 10 is linked to an albumin binding residue via a linker selected from the group consisting of

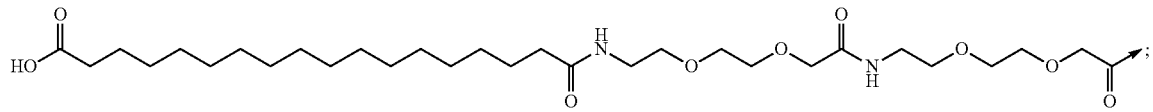

KCNTATCATQRLANFLVHSSNNFG-PILPPTNVGSKTY (SEQ ID No. 17), wherein the lysine residue in position 35 is linked to an albumin binding residue combined with a linker selected from the group consisting of

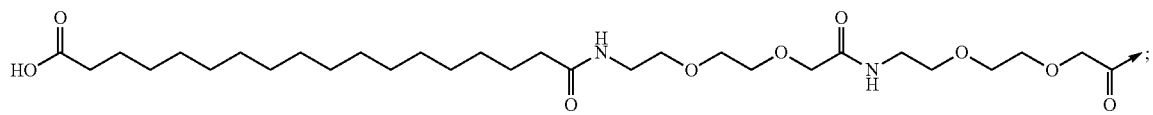

KCNTATCATQRLANFLVRSSNNLGPV-
LPPTNVGSNTYK (SEQ ID No. 18), wherein the lysine
residue in position 38 is linked to an albumin binding residue
via a linker selected from the group consisting of

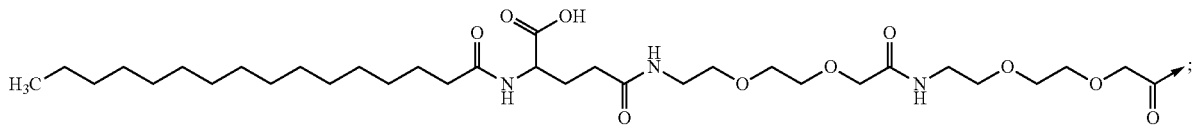

KCNTATCATQRLANFLVKSSNNFG-
PILPPTNVGSNTY (SEQ ID No. 19), wherein the lysine
residue in position 18 is linked to an albumin binding residue
combined with a linker selected from the group consisting of

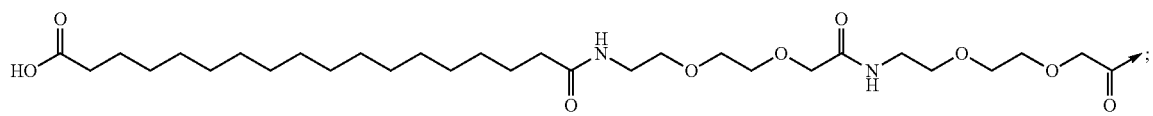

KCNTATCATQRLANFLVHSSNNFGPILP-
KTNVGSNTY (SEQ ID No. 20), wherein the lysine residue
in position 29 is linked to an albumin binding residue combined with a linker selected from the group consisting of

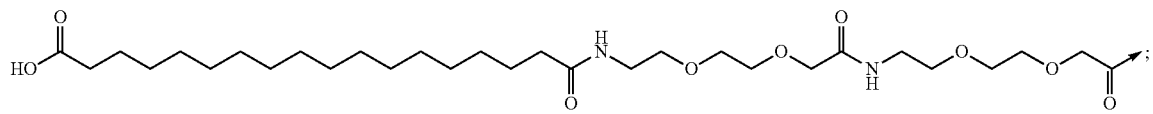

KCNTATCATQRLANFLVKSSNNLGPV-
LPPTNVGSNTY (SEQ ID No. 21), wherein the lysine residue in position 18 is linked to an albumin binding residue via
a linker selected from the group consisting of

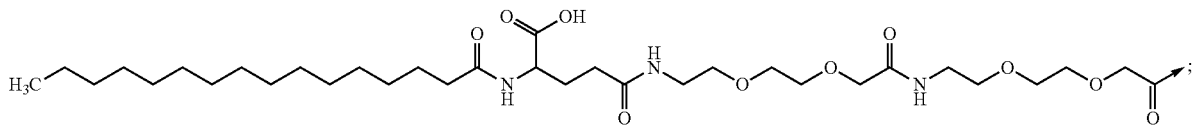

KCNTATCATQKLANFLVRSSNNLGPV-
LPPTNVGSNTY (SEQ ID No. 22), wherein the lysine residue in position 11 is linked to an albumin binding residue
combined with a linker selected from the group consisting of

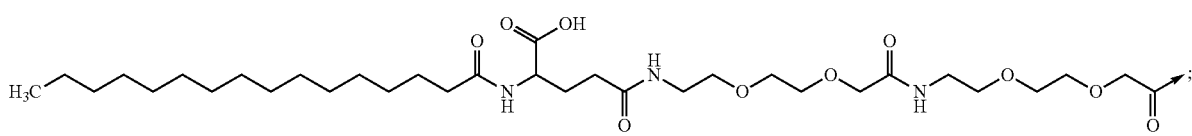

and

KCNTATCATQRLANFLVHSSNNF-GKILPPTNVGSNTY (SEQ ID No. 23), wherein the lysine residue in position 25 is linked to an albumin binding residue combined with a linker selected from the group consisting of

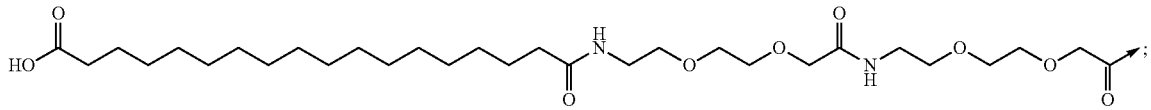

The invention relates in a further aspect to a method for increasing the time of action in a patient of human amylin or an analog thereof, characterized by
a) modifying an amino acid residue in position 2 to 37 by substitution with a lysine residue or a cysteine residue and by linking said lysine residue or cysteine residue to an albumin binding residue or a polyethylene glycol polymer, or
b) linking the lysine residue in position 1 to an albumin binding residue or a polyethylene glycol polymer, or
c) by adding a lysine residue in position 38 wherein said lysine residue is linked to an albumin binding residue or a polyethylene glycol polymer
optionally via a linker; wherein the amino acid numbering conforms with the amino acid numbering in SEQ ID No 1.

The invention relates in a further aspect to a method for increasing the time of action in a patient of human amylin or an analog thereof, characterized by modifying
a) an amino acid residue in position 2 to 37 by substitution with a lysine residue or a cysteine residue and by linking said lysine residue or cysteine residue to an albumin binding residue or a polyethylene glycol polymer, or
b) linking the lysine residue in position 1 to an albumin binding residue or a polyethylene glycol polymer,
optionally via a linker; wherein the amino acid numbering conforms with the amino acid numbering in SEQ ID No 1.

In another aspect, the invention relates to a method wherein the time of action in a patient of human amylin or an analog thereof is increased to more than about 40 hours.

The amylin derivatives can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the therapeutic polypeptide may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the polypeptide may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well-known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracycline chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well-known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well-known and used in the art are, without limitation, *E. coli, Saccharomyces cerevisiae*, or mammalian BHK or CHO cell lines.

Pharmaceutical Compositions

In one aspect of the invention, a pharmaceutical composition comprising a derivative according to the invention and a pharmaceutically acceptable excipient is provided. In a further aspect of the invention, the pharmaceutical composition is suited for parenteral administration.

Another object of the present invention is to provide a pharmaceutical formulation comprising a compound according to the present invention which is present in a concentration from 0.1 mg/ml to 25 mg/ml, and wherein said formulation has a pH from 3.0 to 9.0. The formulation may further comprise a buffer system, preservative(s), tonicity agent(s), chelating agent(s), stabilizers and surfactants. In one embodiment of the invention, the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the invention relates to a pharmaceutical formulation comprising an aqueous solution of a compound according to the present invention, and a buffer, wherein said compound is present in a concentration from 0.1 mg/ml or above, and wherein said formulation has a pH from about 3.0 to about 9.0.

In another embodiment of the invention, the pH of the formulation is from about 3.0 to about 7.0. In another embodiment of the invention, the pH of the formulation is from about 4.0 to about 6.0. In another embodiment of the invention, the pH of the formulation is from about 4.0 to about 5.0. In another embodiment of the invention, the pH of the formulation is from about 7.0 to about 9.5. In another embodiment of the invention, the pH of the formulation is from about 3.0 to about 7.0. In another embodiment of the invention, the pH of the formulation is from about 5.0 to about 7.5. In another embodiment of the invention, the pH of the formulation is from about 7.5 to about 9.0. In another embodiment of the invention, the pH of the formulation is from about 7.5 to about 8.5. In another embodiment of the invention, the pH of the formulation is from about 6.0 to about 7.5. In another embodiment of the invention, the pH of the formulation is from about 6.0 to about 7.0.

In a further embodiment of the invention, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention, the formulation further comprises a pharmaceutically acceptable preservative. In a further embodiment of the invention, the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention, the preservative is present in a concentration from 0.1 mg/ml to 20 mg/ml. In a further embodiment of the invention, the preservative is present in a concentration from 0.1 mg/ml to 5 mg/ml. In a further embodiment of the invention, the preservative is present in a concentration from 5 mg/ml to 10 mg/ml. In a further embodiment of the invention, the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention, the formulation further comprises an isotonic agent. In a further embodiment of the invention, the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment, the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention, the isotonic agent is present in a concentration from 1 mg/ml to 50 mg/ml. In a further embodiment of the invention the isotonic agent is present in a concentration from 1 mg/ml to 7 mg/ml. In a further embodiment of the invention, the isotonic agent is present in a concentration from 8 mg/ml to 24 mg/ml. In a further embodiment of the invention, the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience, reference is made to Remington: *The Science and Practice of Pharmacy*, 19th edition, 1995.

In a further embodiment of the invention, the formulation further comprises a chelating agent. In a further embodiment of the invention, the chelating agent is selected from salts of ethylenediaminetetraacetic acid (EDTA), citric acid, and aspartic acid, and mixtures thereof.

In a further embodiment of the invention, the chelating agent is present in a concentration from 0.1 mg/ml to 5 mg/ml. In a further embodiment of the invention, the chelating agent is present in a concentration from 0.1 mg/ml to 2 mg/ml. In a further embodiment of the invention, the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience, reference is made to Remington: *The Science and Practice of Pharmacy*, 19th edition, 1995.

In a further embodiment of the invention, the formulation further comprises a stabilizer. The use of a stabilizer in pharmaceutical compositions is well-known to the skilled person. For convenience, reference is made to Remington: *The Science and Practice of Pharmacy*, 19th edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essex, U.K.), pp. 491-676; Broadhead et al. (1992) Drug Devel. Ind. Pharm. 18: 1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment, the L-stereoisomer is used. Compositions of the invention may also be formulated with analogs of these amino acids. By "amino acid analog" is intended a derivative of the naturally occurring amino acid that brings about the desired effect of decreasing aggregate formation by the polypeptide during storage of the liquid pharmaceutical compositions of the invention. Suitable arginine analogs include, for example, aminoguanidine, ornithine and N-monoethyl L-arginine, suitable methionine analogs include ethionine and buthionine and suitable cysteine analogs include S-methyl-L cysteine. As with the other amino acids, the amino acid analogs are incorporated into the compositions in either their free base form or their salt form. In a further embodiment of the invention, the amino acids or amino acid analogs are used in a concentration, which is sufficient to prevent or delay aggregation of the protein.

In a further embodiment of the invention, methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention, the formulation further comprises a stabilizer selected from the group of high molecular weight polymers or low molecular compounds. In a further embodiment of the invention, the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention, the formulation further comprises a surfactant. In a further embodiment of the invention, the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives- (e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), nonionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience, reference is made to Remington: *The Science and Practice of Pharmacy,* 19$^{th}$ edition, 1995.

In a further embodiment of the invention, the formulation further comprises protease inhibitors such as EDTA (ethylenediamine tetraacetic acid) and benzamidineHCl, but other commercially available protease inhibitors may also be used. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a compound according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsions, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the compound of the present invention, increase bioavailability, increase solubility, decrease adverse effects, achieve chronotherapy well-known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well-known to those skilled in the art, micelles, liposomes, microspheres, nanoparticulates, liquid crystals and dispersions thereof, L2 phase and dispersions thereof, well-known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of compounds of the present invention, using, for example a metered dose inhaler, dry powder inhaler and a nebulizer, all being devices well-known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well-known to those skilled in the art. Even more preferably are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and super-critical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the compound of the present invention in the form of a nasal or pulmonal spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

The compounds of the present invention can be administered via the pulmonary route in a vehicle, as a solution, suspension or dry powder using any of known types of devices suitable for pulmonary drug delivery. Examples of these comprise, but are not limited to, the three general types of aerosol-generating for pulmonary drug delivery, and may include jet or ultrasonic nebulizers, metered-dose inhalers, or dry powder inhalers (Cf. Yu I, Chien Y W. Pulmonary drug delivery: Physiologic and mechanistic aspects. Crit. Rev Ther Drug Carr Sys 14(4) (1997) 395-453).

Based on standardised testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by:

$$d_a = \sqrt{\frac{\rho}{\rho_a}} d$$

Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well-described and known in the art (cf. Edwards D A, Ben-Jebria A, Langer R and represents a measure of the median value of an aerodynamic particle size distribution. Recent advances in pulmonary drug delivery using large, porous inhaled particles. J Appl Physiol 84(2) (1998) 379-385). Mass median aerodynamic diameter (MMAD) and mass median effective aerodynamic diameter (MMEAD) are used inter-changeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. J Appl Physiol 84(2) (1998) 379-385). MMAD is normally calculated from the measurement made with impactors, an instrument that measures the particle inertial behaviour in air.

In a further embodiment, the formulation could be aerosolized by any known aerosolisation technology, such as nebulisation, to achieve a MMAD of aerosol particles less than 10 μm, more preferably between 1-5 μm, and most preferably between 1-3 μm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the compound of the present invention may optionally be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention, the pharmaceutical formulation comprising the compound of the present invention is stable for more than 6 weeks of usage and for more than 3 years of storage.

In another embodiment of the invention, the pharmaceutical formulation comprising the compound of the present invention is stable for more than 4 weeks of usage and for more than 3 years of storage.

In a further embodiment of the invention, the pharmaceutical formulation comprising the compound of the present invention is stable for more than 4 weeks of usage and for more than 2 years of storage.

In an even further embodiment of the invention, the pharmaceutical formulation comprising the compound of the present invention is stable for more than 2 weeks of usage and for more than 2 years of storage.

In another aspect, the present invention relates to the use of a compound according to the invention for the preparation of a medicament.

In one embodiment, a compound according to the invention is used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, stroke, coronary heart disease and other cardiovascular disorders, inflammatory bowel syndrome, dyspepsia and gastric ulcers.

In another embodiment, a compound according to the invention is used for the preparation of a medicament for delaying or preventing disease progression in type 2 diabetes.

In another embodiment, a compound according to the invention is used for the preparation of a medicament for decreasing food intake, decreasing β-cell apoptosis, increasing β-cell function and β-cell mass, and/or for restoring glucose sensitivity to β-cells.

In one aspect of the invention, the derivative according to the invention is for use as a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers or for delaying or preventing disease progression in type 2 diabetes or for decreasing food intake, decreasing β-cell apoptosis, increasing β-cell function and β-cell mass, and/or for restoring glucose sensitivity to β-cells, is provided.

In a further aspect of the invention, a method for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers or for delaying or preventing disease progression in type 2 diabetes or for decreasing food intake, decreasing β-cell apoptosis, increasing β-cell function and β-cell mass, and/or for restoring glucose sensitivity to β-cells, the method comprising administering to a patient in need of such treatment an effective amount for such treatment of a derivative according to the invention, is provided.

The treatment with a compound according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, gastrin and gastrin analogs.

It should be understood that any suitable combination of the compounds according to the invention with one or more of the above-mentioned compounds and optionally one or more further pharmacologically active substances are considered to be within the scope of the present invention.

FURTHER EMBODIMENTS ACCORDING TO THE INVENTION

1. A derivative of human amylin with SEQ ID No. 1 or an analog thereof, wherein
    a) an amino acid residue in position 2 to 37 has been substituted with a lysine residue or a cysteine residue and wherein such a lysine residue or cysteine residue is linked to an albumin binding residue or a polyethylene glycol polymer, or
    b) the lysine residue in position 1 is linked to an albumin binding residue or a polyethylene glycol polymer,
    optionally via a linker;
    wherein the amino acid numbering conforms with the amino acid numbering in SEQ ID No 1.
2. A derivative according to embodiment 1 of human amylin with SEQ ID No. 1 or an analog thereof, wherein
    an amino acid residue in position 2 to 37 has been substituted with a lysine residue or a cysteine residue and wherein such a lysine residue or cysteine residue is linked to an albumin binding residue or a polyethylene glycol polymer,
    optionally via a linker.
3. The derivative according to any one of the embodiments 1 or 2, wherein the amino acid residue in position 2, 3, 4, 5, or 6 is substituted with a lysine residue or a cysteine residue and wherein such a lysine residue or cysteine residue is linked to an albumin binding residue or a polyethylene glycol polymer, optionally via a linker.
4. The derivative according to any one of the embodiments 1 or 2, wherein the amino acid residue in position 23, 24, 25, 26, 27 or 28 is substituted with a lysine residue or a cysteine residue and wherein such a lysine residue or cysteine residue is linked to an albumin binding residue or a polyethylene glycol polymer, optionally via a linker.
5. The derivative according to any one of the embodiments 1 or 2, wherein the amino acid residue in position 32, 33, 34, 35, 36 or 37 is substituted with a lysine residue or a cysteine residue and wherein such a lysine residue or cysteine residue is linked to an albumin binding residue or a polyethylene glycol polymer, optionally via a linker.
6. The derivative according to any one of the embodiments 1-5, wherein the derivative has from 1-6 amino acid substitutions compared to human amylin.
7. The derivative according to any one of the embodiments 1-5, wherein the derivative has from 1-4 amino acid substitutions compared to human amylin.
8. The derivative according to any one of the embodiments 1-7, wherein -FGAILSS- (SEQ ID No. 2) in position 23 to 29 is changed to -FGPILPP- (SEQ ID No. 3).
9. The derivative according to any one of the embodiments 1-7, wherein -FGAILSS- (SEQ ID No. 2) in position 23 to 29 is changed to -FGEILSS- (SEQ ID No. 4).
10. The derivative according to any one of the embodiments 1-7, wherein -FGAILSS- (SEQ ID No. 2) in position 23 to 29 is changed to -FGDILSS- (SEQ ID No. 5).
11. The derivative according to embodiment 1, wherein the derivative is human amylin of SEQ ID No 1, wherein
    a) an amino acid residue in position 2 to 37 of the human amylin has been substituted with a lysine residue or a cysteine residue and wherein such a lysine residue or cysteine residue is linked to an albumin binding residue or a polyethylene glycol polymer, or
    b) the lysine residue in position 1 of the human amylin is linked to an albumin binding residue or a polyethylene glycol polymer,
    optionally via a linker.
12. The derivative according to embodiment 11, wherein the derivative is human amylin of SEQ ID No 1, wherein
    an amino acid residue in position 2 to 37 of the human amylin has been substituted with a lysine residue or a cysteine residue and wherein such a lysine residue or cysteine residue is linked to an albumin binding residue or a polyethylene glycol polymer, optionally via a linker.
13. The derivative according to any one of the embodiments 11 or 12, wherein the amino acid residue in position 2, 3, 4, 5, or 6 is substituted with a lysine residue or a cysteine residue and wherein such a lysine residue or cysteine residue is linked to an albumin binding residue or a polyethylene glycol polymer, optionally via a linker.
14. The derivative according to any one of the embodiments 11 or 12, wherein the amino acid residue in position 23, 24, 25, 26, 27 or 28 is substituted with a lysine residue or a cysteine residue and wherein such a lysine residue or cysteine residue is linked to an albumin binding residue or a polyethylene glycol polymer, optionally via a linker.
15. The derivative according to any one of the embodiments 11 or 12, wherein the amino acid residue in position 32, 33, 34, 35, 36 or 37 is substituted with a lysine residue or a cysteine residue and wherein such a lysine residue or cysteine residue is linked to an albumin binding residue or a polyethylene glycol polymer, optionally via a linker.
16. The derivative according to any one of the embodiments 11-15, wherein -FGAILSS- (SEQ ID No. 2) in position 23 to 29 is changed to -FGPILPP- (SEQ ID No. 3).
17. The derivative according to any one of the embodiments 11-15, wherein -FGAILSS- (SEQ ID No. 2) in position 23 to 29 is changed to -FGEILSS- (SEQ ID No. 4).

18. The derivative according to any one of the embodiments 11-15, wherein -FGAILSS- (SEQ ID No. 2) in position 23 to 29 is changed to -FGDILSS- (SEQ ID No. 5).
19. The derivative according to any one of the embodiments 1-18, wherein the derivative is linked to a polyethylene glycol polymer.
20. The derivative according to embodiment 19, wherein the poly ethylene glycol polymer is a polyethylene glycol having a molecular weight of at least 30 kD.
21. The derivative according to any one of the embodiments 18-20, wherein the polyethylene glycol polymer is a polyethylene glycol which is branched.
22. The derivative according to any one of the embodiments 1-18, wherein the derivative is linked to an albumin binding residue.
23. The derivative according to embodiment 22, wherein the albumin binding residue is a lipophilic residue.
24. The derivative according to embodiment 22, wherein the albumin binding residue is negatively charged at physiological pH.
25. The derivative according to embodiment 22, wherein the albumin binding residue comprises a group which can be negatively charged.
26. The derivative according to embodiment 25, wherein the albumin binding residue comprises a carboxylic acid group.
27. The derivative according to any one of the embodiments 22-26, wherein the albumin binding residue binds non-covalently to albumin.
28. The derivative according to any one of the embodiments 22-27, wherein the albumin binding residue has a binding affinity towards human serum albumin that is below about 10 µM or below about 1 µM.
29. The derivative according to embodiment 22, wherein the albumin binding residue is selected from the group consisting of a straight chain alkyl group, a branched alkyl group, a group which has an co-carboxylic acid group, and a partially or completely hydrogenated cyclopentanophenanthrene skeleton.
30. The derivative according to embodiment 22, wherein the albumin binding residue is a cibacronyl residue.
31. The derivative according to embodiment 23, wherein the lipophilic residue comprises a partially or completely hydrogenated cyclopentanophenathrene skeleton.
32. The derivative according to embodiment 23, wherein the albumin binding residue has from 6 to 40 carbon atoms, from 8 to 26 carbon atoms or from 8 to 20 carbon atoms.
33. The derivative according to embodiment 23, wherein the albumin binding residue is an acyl group selected from the group comprising $CH_3(CH_2)_rCO-$, wherein r is an integer from 4 to 38, preferably an integer from 4 to 24, more preferred selected from the group comprising $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-CH_3(CH_2)_{18}CO-$, $CH_3(CH_2)_{20}CO-$ and $CH_3(CH_2)_{22}CO-$.
34. The derivative according to embodiment 23, wherein the albumin binding residue is an acyl group of a straight-chain or branched alkane α,ω-dicarboxylic acid.
35. The derivative according to embodiment 23, wherein the albumin binding residue is an acyl group selected from the group comprising $HOOC(CH_2)_sCO-$, wherein s is an integer from 4 to 38, preferably an integer from 4 to 24, more preferred selected from the group comprising $HOOC(CH_2)_{14}CO-$, $HOOC(CH_2)_{16}CO-$, $HOOC(CH_2)_{18}CO-$, $HOOC(CH_2)_{20}CO-$ and $HOOC(CH_2)_{22}CO-$.
36. The derivative according to embodiment 23, wherein the albumin binding residue is a group of the formula $CH_3(CH_2)_vCO-NHCH(COOH)(CH_2)_2CO-$, wherein v is an integer from 10 to 24.
37. The derivative according to embodiment 23, wherein the albumin binding residue is a group of the formula $CH_3(CH_2)_vCO-NHCH((CH_2)_2COOH)CO-$, wherein w is an integer from 8 to 24.
38. The derivative according to embodiment 23, wherein the albumin binding residue is a group of the formula $COOH(CH_2)_xCO-$, wherein x is an integer from 8 to 24.
39. The derivative according to embodiment 23, wherein the albumin binding residue is a group of the formula $-NHCH(COOH)(CH_2)_4NH-CO(CH_2)_yCH_3$, wherein y is an integer from 8 to 18.
40. The derivative according to embodiment 22, wherein the albumin binding residue is a peptide, such as a peptide comprising less than 40 amino acid residues.
41. The derivative according to any one of the embodiments 22-40, wherein the albumin binding residue optionally via a linker is attached via the ε-amino group of a lysine residue.
42. The derivative according to any one of the embodiments 22-40, wherein the albumin binding residue optionally via a linker is attached via a cysteine residue.
43. A pharmaceutical composition comprising a derivative according to any one of the embodiments 1-42, and a pharmaceutically acceptable excipient.
44. The pharmaceutical composition according to embodiment 43, which is suited for parenteral administration.
45. Use of a derivative according to any one of the embodiments 1-42 for the preparation of a medicament.
46. Use of a derivative according to any one of the embodiments 1-42 for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.
47. Use of a derivative according to any one of the embodiments 1-42 for the preparation of a medicament for delaying or preventing disease progression in type 2 diabetes.
48. Use of a derivative according to any one of the embodiments 1-42 for the preparation of a medicament for decreasing food intake, decreasing β-cell apoptosis, increasing β-cell function and β-cell mass, and/or for restoring glucose sensitivity to β-cells.
49. Method for increasing the time of action in a patient of human amylin or an analog thereof, characterized by modifying
   a) an amino acid residue in position 2 to 37 by substitution with a lysine residue or a cysteine residue and by linking such a lysine residue or cysteine residue to an albumin binding residue or a polyethylene glycol polymer, or
   b) linking the lysine residue in position 1 to an albumin binding residue or a polyethylene glycol polymer,
   optionally via a linker; wherein the amino acid numbering conforms with the amino acid numbering in SEQ ID No 1.
50. Method according to embodiment 49, wherein the time of action in a patient of human amylin or an analog thereof is increased to more than about 40 hours.
51. Method according to any one of the embodiments 49 or 50, wherein the human amylin or an analog thereof is as further defined in any one of the embodiments 1-41.

The features disclosed in the foregoing description may, both separately and in any combination thereof, be material for realising the invention in diverse forms thereof.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a formulation described herein as comprising a particular element should be understood as also describing a formulation consisting of that element, unless otherwise stated or clearly contradicted by context).

This invention includes all modifications and equivalents of the subject matter recited in the aspects or claims presented herein to the maximum extent permitted by applicable law.

The present invention is further illustrated in the following representative methods and examples which are, however, not intended to limit the scope of the invention in any way.

Assays

Pharmacological Assay (I)—Experimental Protocol for Efficacy Testing on Appetite with an Amylin Derivative, Using an Ad Libitum Fed Rat Model.

TAC:SPRD @mol rats or Wistar rats from M&B Breeding and Research Centre A/S, Denmark are used for the experiments. The rats have a body weight 200-250 g at the start of experiment. The rats arrive at least 10-14 days before start of experiment with a body weight of 180-200 g. Each dose of derivative is tested in a group of 6-8 rats. A vehicle group of 6-8 rats is included in each set of testing.

When the animals arrive they are housed individually in a reversed light/dark phase (lights off 7:30 am, lights on 7:30 pm), meaning that lights are off during daytime and on during nighttime. Since rats normally initiate food intake when light is removed, and eat the major part of their daily food intake during the night, this set up results in an alteration of the initiation time for food intake to 7:30 am, when lights are switched off. During the acclimatization period of 10-14 days, the rats have free access to food and water. During this period the animals are handled at least 3 times. The experiment is conducted in the rats' home cages. Immediately before dosing the rats are randomised to the various treatment groups (n=6-8) by body weight. They are dosed according to body weight at between 7:00 am and 7:45 am, with a 0.01-3 mg/kg solution administered intraperitoneally (ip), orally (po) or subcutaneously (sc). The time of dosing is recorded for each group. After dosing, the rats are returned to their home cages, where they then have access to food and water. The food consumption is recorded individually continuously by on-line registration or manually every hour for 7 hours, and then after 24 h and sometimes 48 h. At the end of the experimental session, the animals are euthanised.

The individual data are recorded in Microsoft excel sheets. Outliers are excluded after applying the Grubbs statistical evaluation test for outliers, and the result is presented graphically using the GraphPad Prism program.

Pharmacological Assay (II)—Experimental Protocol for Efficacy Testing on Appetite with an Amylin Derivative, Using a Schedule Fed Rat Model.

TAC:SPRD @mol rats or Wistar rats from M&B Breeding and Research Centre A/S, Denmark are used for the experiments. The rats have a body weight 200-250 g at the start of experiment. The rats arrive at least 10-14 days before start of experiment with a body weight of 180-200 g. Each dose of derivative is tested in a group of 6-8 rats. A vehicle group of 6-8 rats is included in each set of testing.

When the animals arrive they are housed individually. At least 7 days prior to onset of study the will start training to a feeding schedule allowing them to have free access to food and water in a scheduled time period between 3 and 7 h. In the remaining period of the day, the rats will not have access to food, but only water. Within a week rats will eat the complete daily ration in the set schedule. Since rats normally initiate food intake when light is removed, and eat the major part of their daily food intake during the night, this set up results allow for monitoring of food intake during day time and will typically mean less variation in the vehicle group compared to an ad libitum fed rat. During the acclimatization period of 10-14 days, the rats have free access to food and water. During this period the animals are handled at least 3 times. The experiment is conducted in the rats' home cages. Immediately before dosing the rats are randomised to the various treatment groups (n=6-8) by body weight. They are dosed according to body weight at between 15 to 30 min prior to given access to food with a 0.01-3 mg/kg solution administered intraperitoneally (ip), orally (po) or subcutaneously (sc). The time of dosing is recorded for each group. After dosing, the rats are returned to their home cages, where they then have access to food and water. The food consumption is recorded individually continuously by on-line registration or manually every hour during the schedule. At the end of the experimental session, the animals are euthanised.

The individual data are recorded in Microsoft excel sheets. Outliers are excluded after applying the Grubbs statistical evaluation test for outliers, and the result is presented graphically using the GraphPad Prism program.

Amylin Receptor Binding Assay

For the receptor binding assay, membranes from the Amylin 3(a)/CRE-luc cells described below were used. The tracer was Tyr-pramlintide iodinated with $^{125}$I in the N-terminal tyrosine. SPA-WGA beads (GE Healthcare RPNQ0001) were incubated in a 96 well Optiplate in a buffer containing 50 mM Hepes, 5 mM $MgCl_2$, 5 mM EGTA, 0.0250% Tween-20, pH 7.4 with membranes, tracer and a dilution series of the amylin analog.

After incubation for 2 hours at room temperature the plates were centrifuged and counted on a Topcounter. The EC50 was calculated as a measure of receptor affinity.

Amylin Luciferase Assay

1. Amylin Assay Outline

It has previously been published (Poyner D R et al 2002, Pharmacological Reviews 54(2) 233-246) that activation of Amylin receptors (coexpression of Calcitonin receptor and receptor activity modifying peptides RAMPs) by Amylin leads to an increase in the intracellular concentration of cAMP. Consequently, transcription is activated at promoters containing multiple copies of the cAMP response element (CRE). It is thus possible to measure Amylin activity by use of a CRE luciferase reporter gene introduced into BHK cells also expressing an Amylin receptor.

2. Construction of an Amylin 3(a)/CRE-luc Cell Line

A BHK570 cell line stably transfected with the human calcitonin receptor (CTa) and a CRE-responsive luciferase reportergene. The cell line was further transfected with RAMP-3, using standard methods. This turns the Calcitonin receptor into an Amylin 3(a) receptor. Methotrexate, Neomycin, and Hygromycin are selection markers for luciferase, the Calcitonin receptor, and RAMP-3, respectively.

3. Amylin Luciferase Assay

To perform activity assays, BHK Amylin 3(a)//CRE-luc cells were seeded in white 96 well culture plates at a density of about 20.000 cells/well. The cells were in 100 µl growth medium (DMEM with 10% FBS, 1% Pen/Strep, 1 mM Na-pyruvate, 250 nM Methotrexate, 500 µg/ml Neomycin, and 400 µg/ml Hygromycin). After incubation overnight at 37° C. and 5% $CO_2$, the growth medium was replaced by 50 µl/well assay medium (DMEM (without phenol red), Glumamax™, 100/a FBS, and 10 mM Hepes, pH 7.4). Further, 50 µl/well of standard or sample in assay buffer were added. After 4 hours incubation at 37° C. and 5% $CO_2$, the assay medium with standard or sample were removed and replaced by 100 µl/well PBS. Further, 100 µl/well LucLite™ was added. The plates were sealed and incubated at room temperature for 30 minutes. Finally, luminescence was measured on a TopCounter (Packard) in SPC (single photon counting) mode.

EXAMPLES

Peptide Synthesis

One method of peptide synthesis was by Fmoc chemistry on a microwave-based Liberty peptide synthesizer (CEM Corp., North Carolina). The resin was Tentagel S RAM with a loading of 0.24 mmol/g. The coupling chemistry was DIC/HOAt in NMP using amino acid solutions of 0.4 M in NMP and a molar excess of 8-10 fold. Coupling conditions was 5 minutes at up to 70° C. Deprotection was with 5% piperidine in NMP at up to 70° C. When a chemical modification of a lysine side chain was desired, the lysine was incorporated as Lys(mtt) and the N-terminal amino acid was protected by treatment with Boc-carbonate. The mtt group was repomed by suspending the resin in neat hexafluoroisopropanol for 20 minutes followed by washing with DCM and NMP. The chemical modification of the lysine was performed either by manual synthesis or by one or more automated steps on the Liberty followed by a manual coupling. Pegylation could also be performed by reaction of purified peptide with e.g. PEG2000-SPA (Nektar) in DMSO. Another method of peptide synthesis was by Fmoc chemistry on an ABI 433 with HBTU coupling. After synthesis the resin was washed with DCM and dried, and the peptide was cleaved from the resin by a 2 hour treatment with TFA/TIS/water (92.5/5/2.5) followed by precipitation with diethylether. After further washing with diethylether and drying, the peptide was redissolved in water at 1-2 mg/ml, pH adjusted to about 4.5, and the disulfide bridge formed by treatment with 1 eq. of $[Pt(IV)$ ethylenediamine$_2Cl_2]Cl_2$ overnight. After lyophilization the peptide was redissolved in 30% acetic acid and purified by standard RP-HPLC on a C18 column using acetonitrile/TFA. Alternatively the lyophilization was omitted and the aqueous solution applied directly to the HPLC column. The identity of the peptide was confirmed by MALDI-MS.

ABBREVIATIONS USED

DMF: N,N dimethylformamide

HBTU: 2-(1H-Benzotriazol-1-yl-)-1,1,3,3 tetramethyluronium hexafluorophosphate

Fmoc: 9H-fluoren-9-ylmethoxycarbonyl

Boc: tert butyloxycarbonyl

Mtt: 4-methyltrityl

DCM: dichloromethane

TIS: truisopropylsilane)

TFA: trifluoroacetic acid

NMP: 1-Methyl-pyrrolidin-2-one

HOAt: 1-Hydroxy-7-azabenzotriazole

DIC: Diisopropylcarbodiimide

Examples 1-28

The derivatives of example 1-28 as described in below table 1 were prepared as described above under "Peptide Synthesis". The derivatives of example 1-28 were tested in the "Amylin luciferase assay" as described above and the results are shown in table 1. The receptor affinities of the derivatives of example 1-28 were tested in the "Amylin receptor binding assay" as described above and the results are shown in table 1. The HPLC elution data in table 1 were measured in an analytical HPLC-system using an acetonitrile/TFA gradient from 10% to 90% over 20 minutes.

As an example, the structure of Example number 1 is shown below. Residues 2, 7, 18, and 37 are expanded to their full structure whereas the remaining amino acids are shown as their one-letter representation. All peptide sequences 1-19 have a disulfide bridge between the cysteines (positions 2 and 7) and all are C-terminal amides.

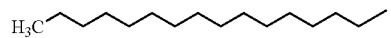
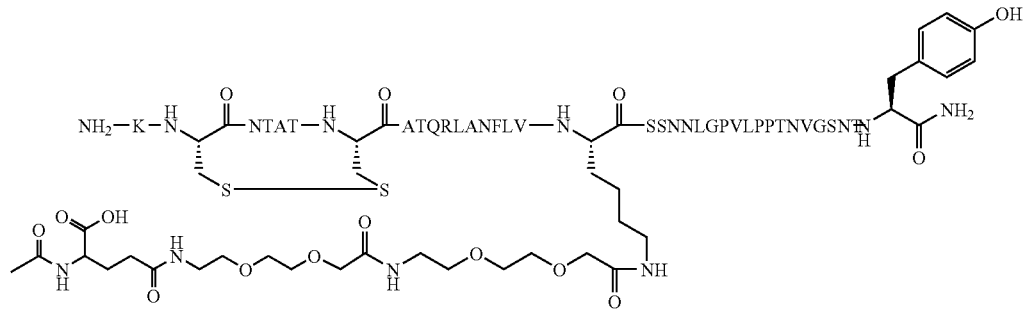

TABLE 1

| NNCD # | Example No. | Seq # (see below table 2) | R-group (see below table 3) | Attachment point | HPLC elution (% acetonitrile) | Potency luciferase assay | Receptor affinity |
|---|---|---|---|---|---|---|---|
| 0002 | 1 | 17 | C | K18-ε | 67% | *** | *** |
| 0004 | 2 | 02 | B | K31-ε | 59% | ** | ** |
| 0005 | 3 | 02 | A | K31-ε | 63% | ** | ** |
| 0006 | 4 | 03 | B | K38-ε | 59% | * | * |
| 0007 | 5 | 03 | A | K38-ε | 62% | * | * |
| 0011 | 6 | 04 | A | K28-ε | 62% | * | * |
| 0013 | 7 | 04 | C | K28-ε | 66% | *** | *** |
| 0016 | 8 | 02 | C | K31-ε | 67% | *** | *** |
| 0018 | 9 | 01 | A | K1-α | 62% | *** | *** |
| 0020 | 10 | 06 | D | K21-ε | 69% | *** | *** |
| 0022 | 11 | 06 | A | K21-ε | 62% | ** | *** |
| 0024 | 12 | 07 | A | K22-ε | 62% | * | *** |
| 0025 | 13 | 07 | E | K22-ε | 68% | ** | ** |
| 0027 | 14 | 08 | A | K16-ε | 58% | * | ** |
| 0028 | 15 | 08 | F | K16-ε | 58% | * | ** |
| 0033 | 16 | 01 | A | K1-ε | 64% | ** | *** |
| 0034 | 17 | 09 | A | K17-ε | 62% | ** | ** |
| 0036 | 18 | 05 | A | K11-ε | 64% | * | ** |
| 0047 | 19 | 10 | A | K14-ε | 62% | * | ** |
| 0050 | 20 | 11 | A | K15-ε | 59% | * | ** |
| 0055 | 21 | 14 | C | K38-ε | 67% | ** | ** |
| 0063 | 22 | 12 | A | K10-ε | 68% | * | ** |
| 0066 | 23 | 13 | A | K35-ε | 68% | * | * |
| 0068 | 24 | 18 | C | K11-ε | 67% | *** | *** |
| 0070 | 25 | 15 | A | K18-ε | 62% | * | ** |
| 0073 | 26 | 16 | A | K29-ε | 62% | ** | *** |
| 0085 | 27 | 19 | A | K25-ε | 61% | ** | *** |
| 0086 | 28 | 01 | PEG2000 | K1-α and K1-ε | 56% | * | * |

TABLE 2

| Seq # | Peptide sequence | SEQ ID No. |
|---|---|---|
| 01 | KCNTATCATQRLANFLVHSSNNFGPILPPTNVGSNTY | SEQ ID No. 24 |
| 02 | KCNTATCATQRLANFLVHSSNNFGPILPPTKVGSNTY | SEQ ID No. 6 |
| 03 | KCNTATCATQRLANFLVHSSNNFGPILPPTNVGSNTYK | SEQ ID No. 7 |
| 04 | KCNTATCATQRLANFLVHSSNNFGPILKPTNVGSNTY | SEQ ID No. 8 |
| 05 | KCNTATCATQKLANFLVHSSNNFGPILPPTNVGSNTY | SEQ ID No. 9 |
| 06 | KCNTATCATQRLANFLVHSSKNFGPILPPTNVGSNTY | SEQ ID No. 10 |
| 07 | KCNTATCATQRLANFLVHSSNKFGPILPPTNVGSNTY | SEQ ID No. 11 |
| 08 | KCNTATCATQRLANFKVHSSNNFGPILPPTNVGSNTY | SEQ ID No. 12 |
| 09 | KCNTATCATQRLANFLKHSSNNFGPILPPTNVGSNTY | SEQ ID No. 13 |

TABLE 2-continued

| Seq # | Peptide sequence | SEQ ID No. |
|---|---|---|
| 10 | KCNTATCATQRLAKFLVHSSNNFGPILPPTNVGSNTY | SEQ ID No. 14 |
| 11 | KCNTATCATQRLANKLVHSSNNFGPILPPTNVGSNTY | SEQ ID No. 15 |
| 12 | KCNTATCATKRLANFLVHSSNNFGPILPPTNVGSNTY | SEQ ID No. 16 |
| 13 | KCNTATCATQRLANFLVHSSNNFGPILPPTNVGSKTY | SEQ ID No. 17 |
| 14 | KCNTATCATQRLANFLVRSSNNLGPVLPPTNVGSNTYK | SEQ ID No. 18 |
| 15 | KCNTATCATQRLANFLVKSSNNFGPILPPTNVGSNTY | SEQ ID No. 19 |
| 16 | KCNTATCATQRLANFLVHSSNNFGPILPKTNVGSNTY | SEQ ID No. 20 |
| 17 | KCNTATCATQRLANFLVKSSNNLGPVLPPTNVGSNTY | SEQ ID No. 21 |
| 18 | KCNTATCATQKLANFLVRSSNNLGPVLPPTNVGSNTY | SEQ ID No. 22 |
| 19 | KCNTATCATQRLANFLVHSSNNFGKILPPTNVGSNTY | SEQ ID No. 23 |

TABLE 3

| R-group | |
|---|---|
| A | |
| B | |
| C | |
| D | |
| E | |
| F | |

In the above table 1 the potency of the derivatives was measured in the "Amylin luciferase assay" as described above under "Assays". In the above table 1 the affinity of the derivatives was measured in the "Amylin receptor binding assay" as described above under "Assays".

In the above table 1 "*" indicates a potency/affinity comparable to pramlintide, "" indicates a potency/affinity somewhat lower than pramlintide, and "*" indicates a potency/affinity much lower than pramlintide.

The invention claimed is:

1. A derivative of human amylin or an analog thereof, wherein a) an amino acid residue in position 2 to 37 has been substituted with a lysine residue or a cysteine residue and wherein said lysine residue or cysteine residue is linked to an albumin binding residue via a linker, or b) the lysine residue in position 1 is linked to an albumin binding residue via a linker, or a lysine residue has been added in position 38 and wherein said lysine residue is linked to an albumin binding residue via a linker;

wherein the combined albumin binding residue and linker is

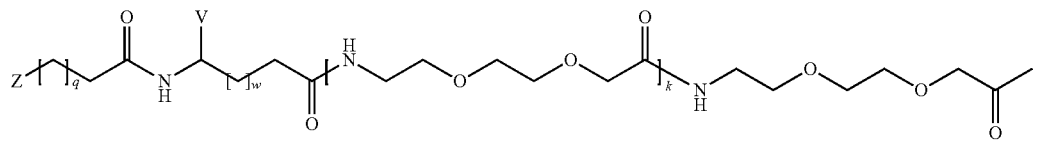

wherein Z is CH₃ or COOH, V is H or COOH, q is 7 to 21, w is 0 to 5, and k is 0 to 5, provided that w and k are not both 1, and wherein the amino acid numbering conforms with the amino acid numbering in SEQ ID No 1.

2. The derivative according to claim 1 which is a derivative of human amylin.

3. The derivative according to claim 1 which is a derivative of a human amylin analog.

4. The derivative according to claim 1, wherein the amino acid residue in position 1, 11, 17, 21, 22, 25, 28, 29 or 31 is substituted with a lysine residue and wherein said lysine residue is linked to an albumin binding residue via a linker.

5. The derivative according to claim 1, wherein the derivative has from 1-6 amino acid substitutions compared to human amylin.

6. The derivative according to claim 1, wherein the derivative has from 1-4 amino acid substitutions compared to human amylin.

7. The derivative according to claim 1, wherein the derivative has a plasma t½ of at least 4 hours.

8. The derivative according to claim 1, wherein the albumin binding residue is a lipophilic residue.

9. A pharmaceutical composition comprising the derivative of human amylin or the analog thereof of claim 1, and a pharmaceutically acceptable excipient.

* * * * *